US006291477B1

(12) United States Patent
Schmidt et al.

(10) Patent No.: US 6,291,477 B1
(45) Date of Patent: Sep. 18, 2001

(54) TETRAHYDROQUINOLINES, PROCESSES FOR THEIR PREPARATION, PHARMACEUTICAL COMPOSITIONS CONTAINING THEM, AND THEIR USE TO PREVENT OR TREAT HYPERLIPOPROTEINAEMIA

(75) Inventors: Gunter Schmidt, Wuppertal; Jürgen Stoltefuss, Haan; Michael Lögers, Wuppertal; Arndt Brandes, Wuppertal; Carsten Schmeck, Wuppertal; Klaus-Dieter Bremm, Recklinghausen; Hilmar Bischoff; Delf Schmidt, both of Wuppertal, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/508,483

(22) PCT Filed: Sep. 7, 1998

(86) PCT No.: PCT/EP98/05658

§ 371 Date: Mar. 10, 2000

§ 102(e) Date: Mar. 10, 2000

(87) PCT Pub. No.: WO99/15504

PCT Pub. Date: Apr. 1, 1999

(30) Foreign Application Priority Data

Sep. 19, 1997 (DE) .............................. 197 41 399

(51) Int. Cl.[7] ...................... A61K 31/505; A61K 31/47; C07D 401/00; C07D 215/20
(52) U.S. Cl. ...................... 514/311; 514/256; 514/314; 544/333; 546/167; 546/179

(58) Field of Search ................................... 514/311, 314, 514/256; 544/333; 546/167, 179

(56) References Cited

U.S. PATENT DOCUMENTS

| 5,169,857 | 12/1992 | Angerbauer et al. | 514/344 |
|---|---|---|---|
| 5,401,746 | 3/1995 | Angerbauer et al. | 514/277 |
| 5,506,219 | 4/1996 | Robl | 514/89 |
| 6,069,148 | * 5/2000 | Schmidt | 514/277 |

FOREIGN PATENT DOCUMENTS

| 196 27 419 | 1/1998 | (DE) . |
| 197 09 125 | 9/1998 | (DE) . |
| 0 444 533 | 9/1991 | (EP) . |
| 0 818 448 | 1/1998 | (EP) . |

OTHER PUBLICATIONS

G. N. Tyurenkova et al., *Khim. Geterotsikl. Soedin.*, 6:1118–1120 (967).
A. Patton, et al., *J. Organic Chemistry*, 44: 4749–4752 (1979).
J. Dinchuk et al., *Biochim. Biophys. Acta*, 1255: 301–310 (1995).

* cited by examiner

*Primary Examiner*—D. Margaret Seaman
(74) *Attorney, Agent, or Firm*—Norris McLaughlin & Marcus

(57) ABSTRACT

The tetrahydroquinolines can be prepared by condensing appropriately substituted tetrahydroquinoline aldehydes with suitable substances and subsequently varying the substituents present by customary methods. The tetrahydroquinolines are suitable as active compounds in medicaments, in particular in medicaments for the treatment of arteriosclerosis and dyslipidaemias.

17 Claims, No Drawings

TETRAHYDROQUINOLINES, PROCESSES FOR THEIR PREPARATION, PHARMACEUTICAL COMPOSITIONS CONTAINING THEM, AND THEIR USE TO PREVENT OR TREAT HYPERLIPOPROTEINAEMIA

This application is a 371 of PCT/EP98/05658, which was filed on Sep. 7, 1998.

The present invention relates to tetrahydroquinolines, to processes for their preparation and to their use in medicaments.

The publication US-5 169 857-A2 discloses 7-(polysubstituted pyridyl)-6-heptenoates for treating arteriosclerosis, lipoproteinaemia and hyperproteinaeria. Moreover, the preparation of 7-(4-aryl-3-pyridyl)-3,5-dihydroxy-6-heptenoates is described in the publication EP-325 130A2. Furthermore, the compound 5(6H)-quinolones,3-benzyl-7,8-dihydro-2,7,7-trimethyl-4-phenyl, is known from the publication Khim. Geterotsikl. Soedin. (1967), (6), 1118–1120.

The present invention relates to tetrahydroquinolines of the general formula (I),

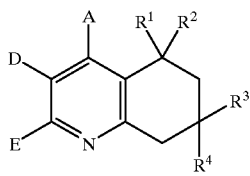

(I)

in which
A represents phenyl which is optionally substituted up to 2 times by identical or different substituents from the group consisting of halogen, trifluoromethyl and straight-chain or branched alkyl or alkoxy having in each case up to 3 carbon atoms,
D represents a radical of the formula

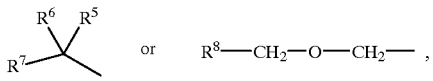

in which
$R^5$ and $R^6$ together form a carbonyl group (=O),
or
$R^5$ represents hydrogen
and
$R^6$ represents halogen or hydroxyl,
or
$R^5$ and $R^6$ represent hydrogen,
$R^7$ and $R^8$ are identical or different and represent phenyl, naphthyl, benzothiazolyl, quinolyl, pyrimidyl or pyridyl which are optionally substituted up to 4 times by identical or different substituents from the group consisting of halogen, trifluoromethyl, nitro, cyano, trifluoromethoxy, or by a radical of the formula —$SO_2$—$CH_3$ or $NR^9R^{10}$,
in which
$R^9$ and $R^{10}$ are identical or different and represent hydrogen or straight-chain or branched alkyl having up to 3 carbon atoms,
E represents cycloalkyl having 3 to 6 carbon atoms, or represents straight-chain or branched alkyl having up to 8 carbon atoms, $R^1$ represents hydroxyl,
and
$R^2$ represents hydrogen or represents methyl,
$R^3$ and $R^4$ are identical or different and represent straight-chain or branched alkyl having up to 3 carbon atoms,
or
$R^3$ and $R^4$ together form a spiro-linked alkyl chain having 2 to 4 carbon atoms,
and their salts and N-oxides.

The tetrahydroquinolines according to the invention can also be present in the form of their salts. In general, salts with organic or inorganic bases or acids may be mentioned here.

In the context of the present invention, preference is given to physiologically acceptable salts. Physiologically acceptable salts of the compounds according to the invention can be salts of the substances according to the invention with mineral acids, carboxylic acids or sulphonic acids. Particular preference is given, for example, to salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Particular preference is given, for example, to sodium, potassium, magnesium or calcium salts, and to ammonium salts, which are derived from ammonia, or organic amines, such as, for example, ethylamine, di- or triethylamine, di- or triethanolamine, dicyclohexylamine, dimethylaminoethanol, arginine, lysine, ethylenediamine or 2-phenylethylamine.

The compounds according to the invention can exist in stereoisomeric forms which are either like image and mirror image (enantiomers), or which are not like image and mirror image (diastereomers). The invention relates both to the enantiomers or diastereomers and to their respective mixtures. These mixtures of enantiomers and diastereomers can be separated into the stereoisomerically uniform components in a known manner.

Preference is given to compounds of the general formula (I) according to the invention
in which
A represents phenyl which is optionally substituted up to 2 times by identical or different substituents from the group consisting of fluorine. chlorine, trifluoromethyl, methyl, ethyl, methoxy and ethoxy,
D represents a radical of the formula

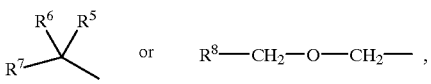

in which
$R^5$ and $R^6$ together form a carbonyl group (=O),
or
$R^5$ represents hydrogen
and
$R^6$ represents fluorine or hydroxyl,
or
$R^5$ and $R^6$ represent hydrogen,
$R^7$ and $R^8$ are identical or different and represent phenyl, naphthyl, benzothiazolyl, quinolyl, pyrimidyl or pyridyl, which are optionally substituted up to 3 times by identical or different substituents from the group consisting of fluorine, chlorine, bromine, trifluoromethyl, nitro, cyano, trifluoromethoxy, amino or dimethylamino, E represents cyclopropyl, cyclobutyl, cyclopentyl or represents straight-chain or branched alkyl having up to 6 carbon atoms, $R^1$ represents hydroxyl, and $R^2$ represents hydrogen or represents methyl, $R^3$ and $R^4$ are identical or different and represent methyl, or $R^3$ and $R^4$ together form a spiro-linked cyclopropyl, cyclobutyl or cyclopentyl ring, and their salts and N-oxides.

Particular preference is given to compounds of the general formula (I) according to the invention in which A represents phenyl which is optionally substituted up to 2 times by identical or different substituents from the group consisting of fluorine, chlorine, trifluoromethyl, methyl, methoxy and ethoxy, D represents a radical of the formula

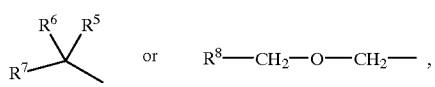

in which $R^5$ and $R^6$ together form a carbonyl group (=O), or $R^5$ represents hydrogen and $R^6$ represents fluorine or hydroxyl or $R^5$ and $R^6$ represent hydrogen, $R^7$ and $R^8$ are identical or different and represent phenyl, naphthyl, benzothiazolyl, quinolyl, pyrimidyl or pyridyl which are optionally substituted up to 3 times by identical or different substituents from the group consisting of fluorine, chlorine, bromine, trifluoromethyl, nitro, cyano, trifluoromethoxy, amino and dimethylamino, E represents cyclopropyl or cyclopentyl, or represents straight-chain or branched alkyl having up to 3 carbon atoms, $R^1$ represents hydroxyl and $R^2$ represents hydrogen or represents methyl, $R^3$ and $R^4$ are identical or different and represent methyl, or $R^3$ and $R^4$ together form a spiro-linked cyclopropyl, cyclobutyl or cyclopentyl ring, and their salts and N-oxides.

Moreover, processes for preparing the compounds of the general formula (I) according to the invention have been found which are characterized in that

[A] in the case that D represents the radical

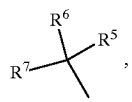

in compounds of the general formula (II)

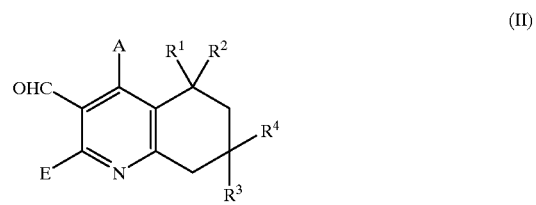

in which

A, E, $R^1$, $R^2$, $R^3$ and $R^4$ are as defined above, the substituent D is synthesized in inert solvents using organometallic reagents in a Grignard, Wittig or organolithium reaction, or, in the case that D represents the radical of the formula $R^8$—$CH_2$—O—$CH_2$, in which $R^8$ is as defined above,

[B] either compounds of the general formula (III)

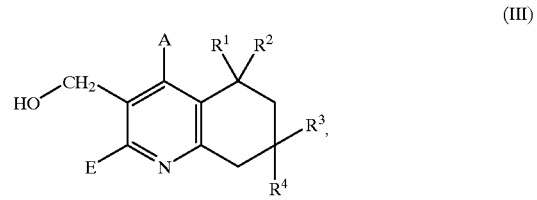

in which

A, E, $R^1$, $R^2$, $R^3$ and $R^4$ are as defined above are reacted with compounds of the general formula (IV)

$R^8$—$CH_2$—Z  (IV), in which $R^8$ is as defined above, and

Z represents halogen, preferably chlorine or bromine, in inert solvents, if appropriate in the presence of a base and/or an auxiliary, or

[C] compounds of the general formula (III) are first converted, by reaction with compounds of the general formula (V)

in which $R^{11}$ represents straight-chain alkyl having up to 4 carbon atoms, into the compounds of the general formula (VI)

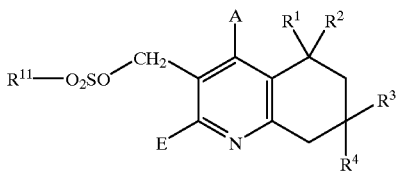
(VI)

in which
A, E, $R^1$, $R^2$, $R^3$, $R^4$ and $R^{11}$ are as defined above,
and subsequently reacted with compounds of the general formula (VII)

$R^8—CH_2—OH$ (VII), in which
$R^8$ is as defined above,
and, if appropriate, protective groups are cleaved off,
or
[D] in the case of the compounds of the general formula (Ia)

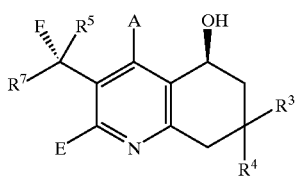
(Ia)

in which
A, E, $R^3$, $R^4$, $R^5$ and $R^6$ are as defined above,
compounds of the general formula (VIII)

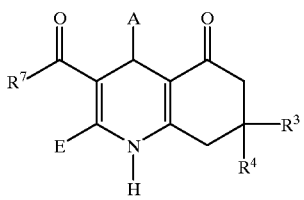
(VIII)

in which
A, E, $R^3$, $R^4$ and $R^7$ are as defined above,
are first oxidized to the compounds of the general formula (IX)

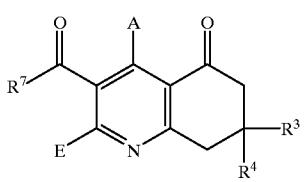
(IX)

in which
$R^3$, $R^4$, $R^7$, A and E are as defined above,
these are, in a next step, converted by asymmetric reduction into the compounds of the general fornula (X)

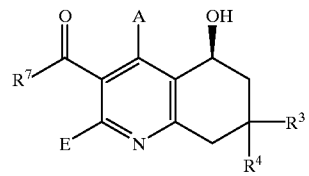
(X)

in which
$R^3$, $R^4$, $R^7$, A and E are as defined above,
these are then converted, by introduction of a hydroxyl-protective group, into the compounds of the general formula (XI)

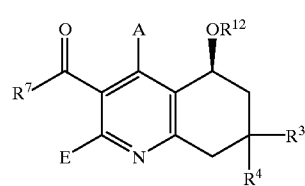
(XI)

in which
$R^3$, $R^4$, $R^7$, A and E are as defined above
and
$R^{12}$ represents a hydroxyl-protective group, preferably a radical of the formula $—SiR^{13}R^{14}R^{15}$,
in which
$R^{13}$, $R^{14}$ and $R^{15}$ are identical or different and represent $C_1$–$C_4$-alkyl,
from which compound, in a subsequent step, the compounds of the general formula (XII)

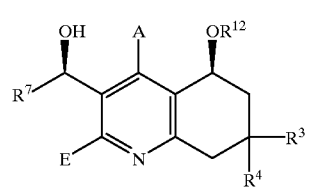
(XII)

in which
$R^3$, $R^4$, $R^7$, $R^{12}$, A and E are as defined above,
are prepared by diastereoselective reduction,
and subsequently, by introducing the fluorine substituent with fluorinating agents, such as, for example, DAST and $SF_4$ derivatives, the compounds of the general formula (XIII)

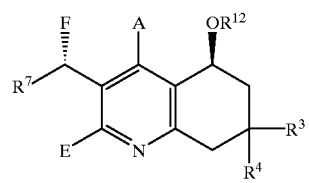
(XIII)

in which
$R^3$, $R^4$, $R^7$, $R^{12}$, A and E are as defined above,
are prepared,
and the hydroxyl-protective group is subsequently cleaved off by customary methods, and, if appropriate, the substituents listed under D, E and/or $R^1$ and $R^2$ are varied or introduced by customary methods.
The processes according to the invention can be illustrated in an exemplary manner by the following schemes:
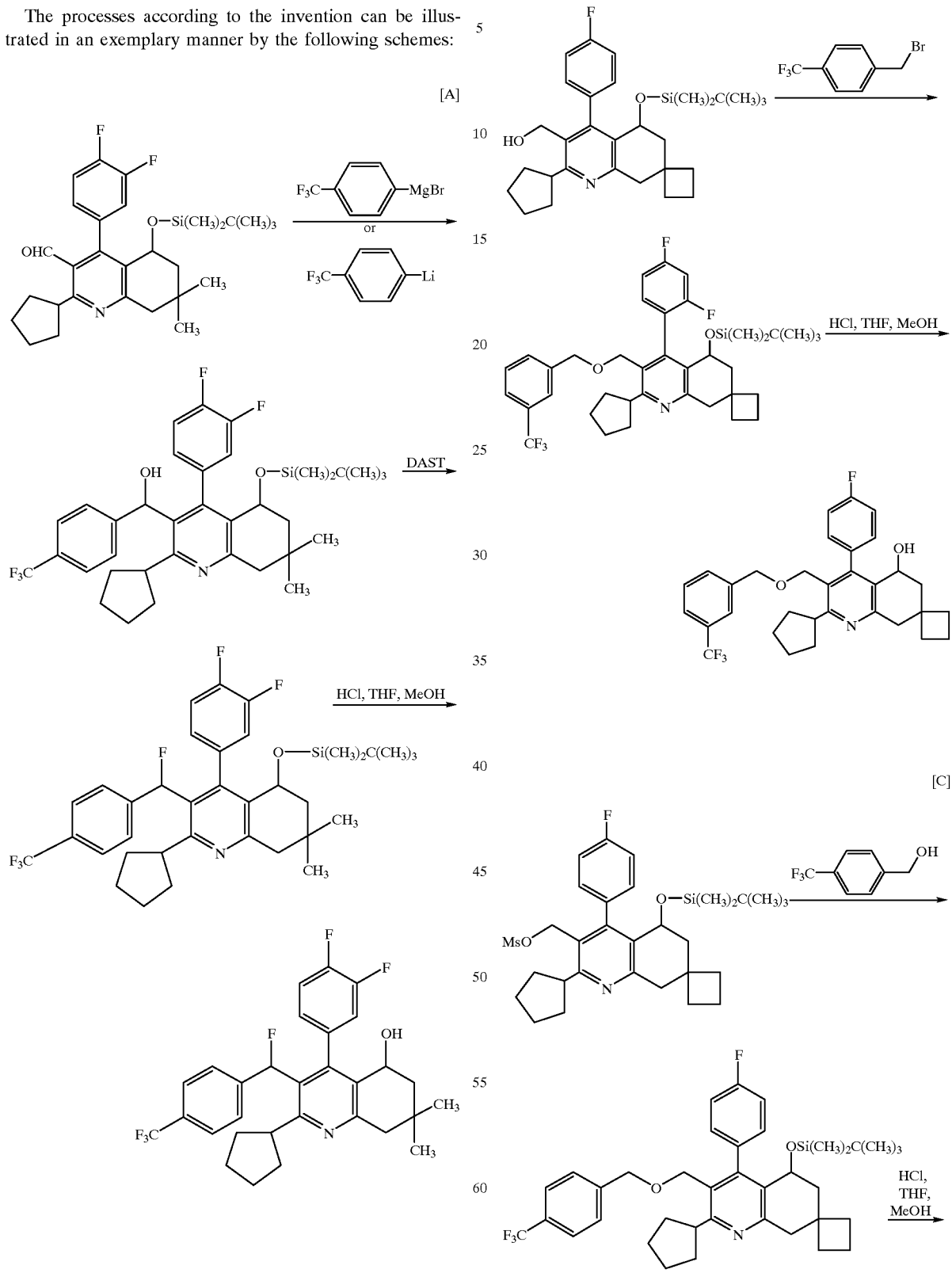

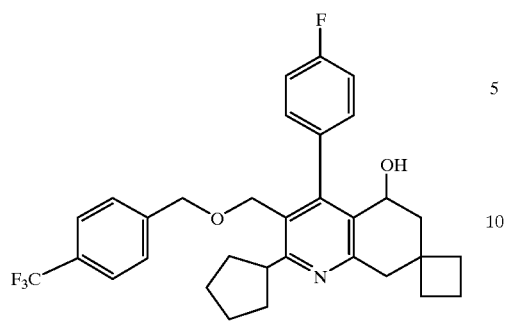
Ms = mesylate
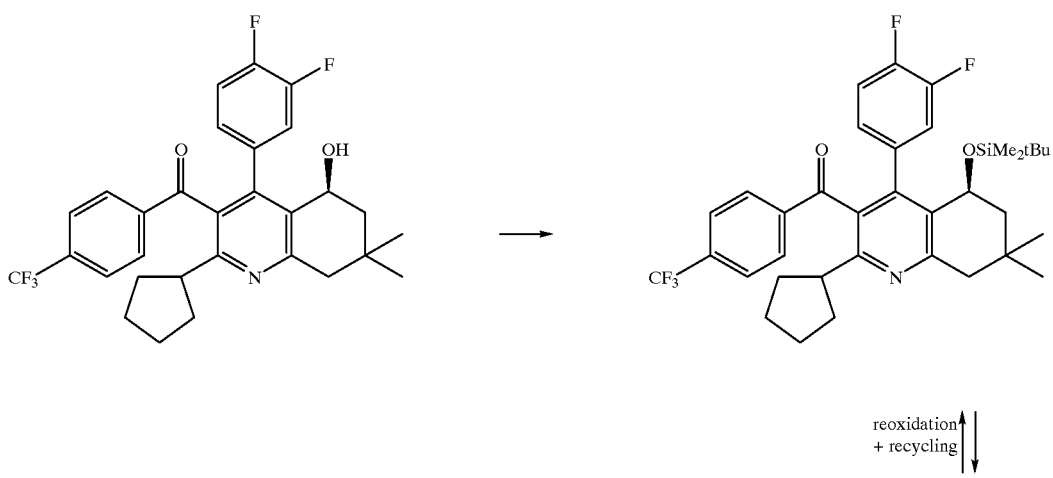
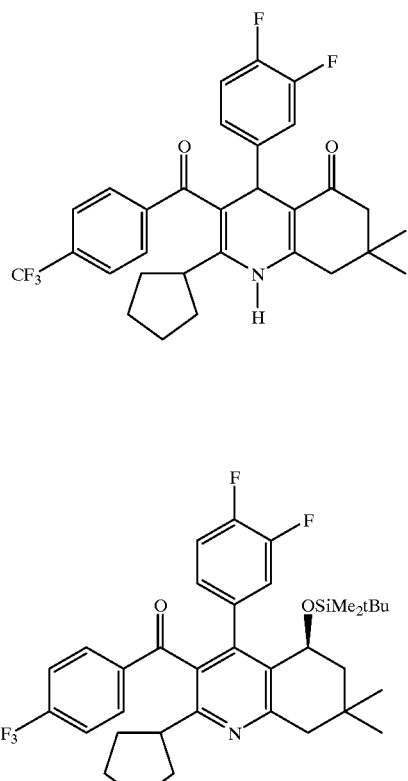
reoxidation + recycling

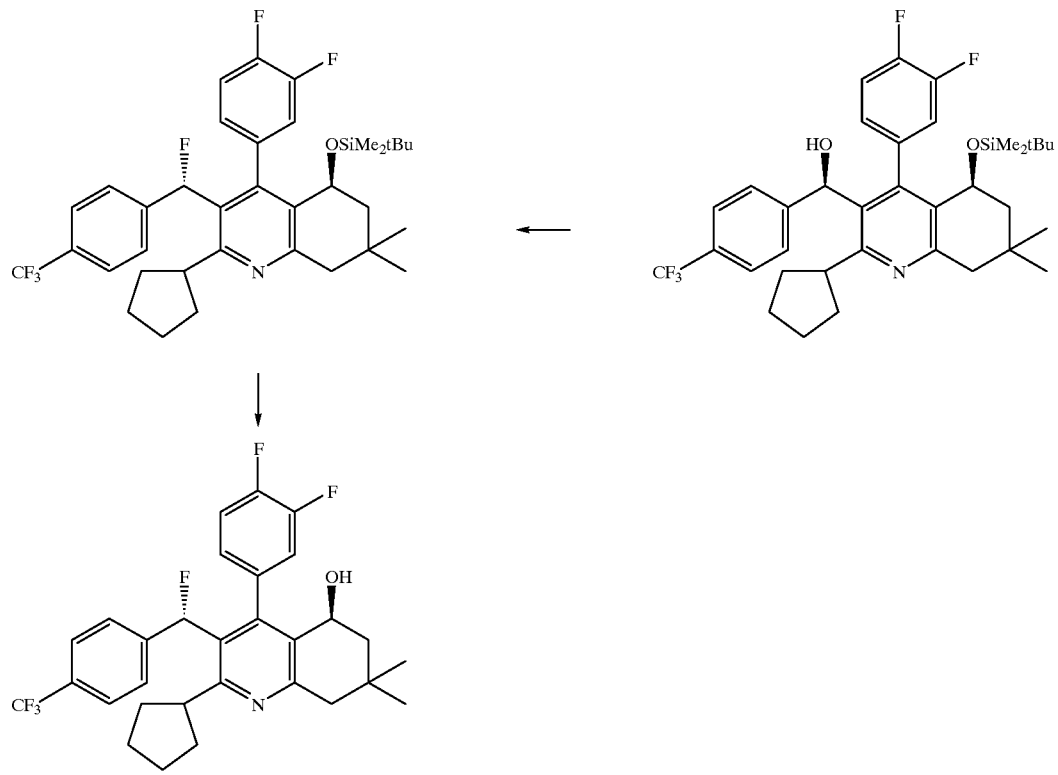

Suitable solvents for all processes are ethers such as diethyl ether, dioxane, tetrahydrofuran, glycol dimethyl ether, or hydrocarbons such as benzene, toluene, xylene, hexane, cylcohexane or mineral oil fractions, or halogenated hydrocarbons such as dichloromethane, trichloromethane, carbon tetrachl oride, dichloroeth ylene, trichloroethylene or chlorobenzene, or ethyl acetate, or triethylamne, pyridine, dimethyl sulphoxide, dimethylformamide, hexamethylphosphoric triaide, acetonitrile, acetone or nitromethane. It is also possible to use mixtures of the solvents mentioned. Preference is given to dichloromethane.

Suitable bases for the in dividual steps are the customary strongly basic compounds. These preferably include organolithium compounds such as, for example, N-butyllithium, sec-butyllithium, tertbutyllithium or phenyllithium, or amides such as, for example, lithium diisopropylamide, sodium amide or potassium amide, or lithium hexamethylsilylamide, or alkali metal hydrides such as sodium hydride or potassium hydride. Particular preference is given to using N-butyllithium, sodium hydride or lithium diisopropylamide.

Suitable for the processes [B] and [C] are furthermore the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium bicarbonate. Particular preference is given to using sodium hydride or potassium hydroxide.

Suitable organometallic reagents are, for example, systems such as the appropriate Wittig reagents, for example Mg/bromobenzotrifluoride, and the appropriate organolithium compounds, for example p-trifluoromethylphenyllithium.

The reductions are generally carried out using reducing agents, preferably those which are suitable for reducing ketones to hydroxyl compounds. Particularly suitable here is the reduction with metal hydrides or complex metal hydrides in inert solvents, if appropriate in the presence of a trialkylborane. The reduction is preferably carried out using complex metal hydrides such as, for example, lithium borohydride, sodium borohydride, potassium borohydride, zinc borohydride, lithium trialkylborohydride, diisobutylaluminium hydride or lithium aluminium hydride. The reduction is very particularly preferably carried out using diisobutylaluminium hydride and sodium borohydride.

The reducing agent is generally employed in an amount of from 1 mol to 6 mol, preferably from 1 mol to 4 mol based on 1 mol of the compounds to be reduced.

The reduction generally proceeds in a temperature range of from −78° C. to +50° C., preferably from −78° C. to 0° C. in the case of DIBAH, from 0° C. to room temperature in the case of $NABH_4$, particularly preferably at −78° C., in each case depending on the choice of the reducing agent and the solvent.

The reduction generally proceeds at atmospheric pressure; however, it is also possible to operate under elevated or reduced pressure.

The hydrogenation is carried out by customary methods using hydrogen in the presence of noble metal catalysts, such as, for example, Pd/C, Pt/C or Raney nickel in one of the abovementioned solvents, preferably in alcohols such as, for example, methanol, ethanol or propanol, in a temperature range of from −20° C. to +100° C., preferably from 0° C. to +50° C., under atmospheric pressure or superatmospheric pressure.

The protective group is generally removed in one of the abovementioned alcohols and THF, preferably methanol/THF in the presence of hydrochloric acid in a temperature range of from 0° C. to 50° C., preferably at room temperature, and atmospheric pressure. In particular cases, preference is given to cleaving off the protective group with tetrabutylammonium fluoride (TBAF) in THF.

In the context of the definition given above, hydroxyl-protective group generally represents a protective group from the series: trimethylsilyl, triisopropylsilyl, tert butyldimethylsilyl, benzyl, benzyloxycarbonyl, 2-nitrobenzyl, 4-nitrobenzyl, tert butyloxycarbonyl, allyloxycarbonyl, 4-methoxybenzyl, 4-methoxybenzyloxycarbonyl, tetrahydropyranyl, formyl, acetyl, trichloroacetyl, 2,2,2-trichloroethoxycarbonyl, methoxyethoxymethyl, [2-(trimethylsilyl)ethoxy]methyl, benzoyl, 4-methylbenzoyl, 4-nitrobenzoyl, 4-fluorobenzoyl, 4-chlorobenzoyl or 4-methoxybenzoyl. Preference is given to tetrahydiopyranyl, tert-butyldimethylsilyl and triisopropylsilyl. Particular preference is given to tert-butyldimethylsilyl.

Suitable solvents for the individual steps are ethers such as diethyl ether, dioxane, tetrahydrofuran, glycol dimethyl ether, diisopropyl ether or hydrocarbons such as benzene, toluene, xylene, hexane, cyclohexane or mineral oil fractions, or halogenated hydrocarbons such as dichloromethane, trichloromethane, carbon tetrachloride, dichloroethylene, trichloroethylene or chlorobenzene. It is also possible to use mixtures of the solvents mentioned.

Suitable oxidizing agents for preparing the compounds of the general formula (IX) are, for example, nitric acid, acid, cerium(IV)ammonium nitrate, 2,3-dichloro-5,6-dicyanobenzoquinone, pyridinium chlorochromate (PCC), pyridinium chlorochromate on basic alumina, osmium tetroxide and manganese dioxide. Preference is given to manganese dioxide and nitric acid.

The oxidation is carried out in one of the abovementioned chlorinated hydrocarbons and water. Preference is given to dichloromethane and water.

The oxidizing agent is employed in an amount of from 1 mol to 10 mol, preferably from 2 mol to 5 mol, based on 1 mol of the compounds of the general formula (VIII).

The oxidation generally proceeds at a temperature of from $-50°$ C. to $+100°$ C., preferably from $0°$ C. to room temperature.

The oxidation generally proceeds at atmospheric pressure. However, it is also possible to carry out the oxidation under elevated or reduced pressure.

The asymmetric reduction to the compounds of the general formula (X) is generally carried out in one of the abovementioned ethers or toluene, preferably tetrahydrofuran and toluene.

The reduction is generally carried out using enantiomerically pure 1R,2S-aminoindanol and borane complexes such as $BH_3 \times THF$, $BH_3 \times DMS$ and $BH_3 \times (C_2H_5)_2NC_6H_5$. Preference is given to the system borane diethylaniline/1R,2S-aminoindanol.

The reducing agent is generally employed in an amount of from 1 mol to 6 mol, preferably from 1 mol to 4 mol based on 1 mol of the compounds to be reduced.

The reduction generally proceeds at a temperature of from $-78°$ C. to $+50°$ C., preferably from $0°$ C. to $30°$ C.

The reduction generally proceeds at atmospheric pressure; however, it is also possible to operate under elevated or reduced pressure.

The hydroxyl-protective group is introduced in one of the abovementioned hydrocarbons, dimethylformamide or THF, preferably in toluene in the presence of lutidine in a temperature range of from $-20°$ C. to $+50°$ C., preferably from $-5°$ C. to room temperature and atmospheric pressure.

Reagents for introducing the silyl protective group are, in general, tert-butyldimethylsilyl chloride or tert-butyldimethylsilyl trifluoromethanesulphonate. Preference is given to tert-butyldimethylsilyl trifluoromethansulphonate.

The reduction to the compounds of the general formula (XII) proceeds in one of the abovementioned hydrocarbons, preferably toluene.

The reduction for preparing the compounds of the general formula (XII) is generally carried out using customary reducing agents, preferably those which are suitable for reducing ketones to hydroxyl compounds are. Particularly suitable for this purpose is the reduction with metal hydrides or complex metal hydroxides in inert solvents, if appropriate in the presence of a trialkylborane. The reduction is preferably carried out using complex metal hydrides such as, for example, lithium borohydride, sodium borohydride, potassium borohydride, zinc borohydride, lithium trialkylborohydride, diisobutylaluminium hydride, sodium bis-(2-methoxyethoxy)aluminium hydride or lithium aluminium hydride. Very particularly preferably, the reduction is carried out using sodium bis-(2-methoxyethoxy)-aluminium hydride.

The reducing agent is generally employed in an amount of from 1 mol to 6 mol, preferably from 1 mol to 3 mol based on 1 mol of the compounds to be reduced.

The reduction generally proceeds at a temperature of from $-20°$ C. to $+110°$ C., preferably from $0°$ C. to room temperature.

The reduction generally proceeds at atmospheric pressure; however, it is also possible to operate under elevated or reduced pressure.

In the reduction to the compounds of the general formula (XII), small residues of the wrong diastereomer remain in the mother liquor. These residues can be reoxidized with customary oxidizing agents such as, for example, pyridinium chlorochromate (PCC) or activated manganese dioxide, in particular with activated manganese dioxide to protected (XI) and thus be recycled into the synthesis cycle without loss of yield.

The fluorine substituent is generally introduced in one of the abovementioned hydrocarbons or methylene chloride, preferably in toluene and under an atmosphere of protective gas.

$SF_4$ derivatives are generally understood to be diethylaminosulphur trifluoride (DAST) or 2,2'-bisfluoro-substituted amines such as, for example, diethyl-1,2,3,3,3-hexafluoropropylamine.

The reaction generally proceeds at a temperature of from $-78°$ C. to $100°$ C., preferably, in the case of the diethylaminosulphur trifluoride, at from $-78°$ C. to RT and, in the case of the diethyl-1,1,2,3,3,3-hexafluoropropylamine, at from room temperature to $80°$ C.

The protective group is generally cleaved off in one of the abovementioned alcohols and TBF, preferably methanol/THF in the presence of hydrochloric acid in a temperature range of from $0°$ C. to $50°$ C., preferably at room temperature, and atmospheric pressure. In particular cases, preference is given to cleaving off the protective group with tetrabutylammonium fluoride (TBAF) in THF at room temperature.

Derivatizations which may be mentioned by way of example are the following reaction types:

oxidations, reductions, hydrogenations, halogenation, Wittig/Grignard reactions and amidations/sulphoamidations.

Suitable bases for the individual steps are the customary strongly basic compounds. These preferably include organolithium compounds such as, for example, n-butyllithium, sec-butyllithium, tertbutyllithium or phenyllithium, or amides such as, for example, lithium diisopropylamide, sodium amide or potassium amide, or lithium hexamethylsilylamide, or alkali metal hydrides such as sodium hydride or potassium hydride. Particular preference is given to using N-butyllithium, sodium hydride or lithium diisopropylamide.

Suitable bases are furthermore the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium bicarbonate. Particular preference is given to using sodium hydroxide or potassium hydroxide.

Suitable solvents for the individual reaction steps are also alcohols such as methanol, ethanol, propanol, butanol or tertbutanol. Preference is given to tertbutanol.

If required, it is necessary to carry out some reaction steps under an atmosphere of protective gas The halogenations are generally carried out in one of the abovementioned chlorinated hydrocarbons, and preference is given to methylene chloride.

Suitable halogenating agents are, for example, diethylamino-sulphur trifluoride (DAST), morpholino-sulphur trifluoride or $SOCl_2$.

The halogenation generally proceeds in a temperature range of from −78° C. to +50° C., preferably from −78° C. to 0° C., in each case depending on the choice of halogenating agent and solvent.

The halogenation generally proceeds at atmospheric pressure; however, it is also possible to operate under elevated or reduced pressure.

The compounds of the general formulae (II) and (III) are novel and can be prepared by preparing,
by reacting the compounds of the general formula (XIV)

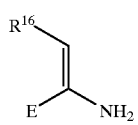

(XIV)

in which
E is as defined above
and
$R^{16}$ represents $C_1$–$C_4$-alkoxycarbonyl or aryl (D=aryl)
with aldehydes of the general formula (XV)

 (XV), in which
A is as defined above,
and compounds of the general formula (XVI)

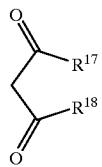

(XVI)

in which
$R^{17}$ and $R^{18}$ together with a carbonyl group have the abovementioned scope of $R^1$ and $R^2$, the compounds of the general formula (XVII)

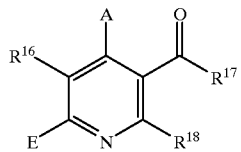

(XVII)

in which
A, E, $R^{16}$, $R^{17}$ and $R^{18}$ are as defined above
and, in the case of the compounds of the general formula (III), then carrying out a reduction, as described above, to give the hydroxymethyl function,
and, in a last step, converting the alkoxycarbonyl group ($R^{16}$) by a reduction-oxidation sequence into an aldehyde group.

Suitable solvents for the oxidation are ethers such as diethyl ether, dioxane, tetrahydrofuran, glycol dimethyl ether, or hydrocarbons such as benzene, toluene, xylene, hexane, cyclohexane or mineral oil fractions, or halogenated hydrocarbons such as dichloromethane, trichloromethane, carbon tetrachloride, dichloroethylene, trichloroethylene or chlorobenzene, or ethyl acetate, or triethylamine, pyridine, dimethyl sulphoxide, dimethylformamide, hexamethylphosphoric triamide, acetonitrile, acetone or nitromethane. It is also possible to use mixtures of the solvents mentioned. Preference is given to methylene chloride.

Suitable oxidizing agents are, for example, cerium(IV) ammonium nitrate, 2,3-dichloro-5,6-dicyano-benzoquinone, pyridinium chlorochromate (PCC), pyridinium chlorochromate on basic alumina, osmium tetroxide and manganese dioxide. Preference is given to sulphur trioxide-pyridine complex in DMSO/methylene chloride and pyridinium chlorochromate on basic alumina.

The oxidizing agent is employed in an amount of from 1 mol to 10 mol, preferably from 2 mol to 5 mol, based on 1 mol of the compounds of the general formula (XVII).

The oxidation generally proceeds in a temperature range of from −50° C. to +100° C., preferably from 0° C. to room temperature.

The oxidation generally proceeds at atmospheric pressure. However, it is also possible to carry out the oxidation under elevated or reduced pressure.

The compounds of the general formulae (IV), (V), (VII), (XIV), (XV) and (XVI) are known per se or can be prepared by customary methods.

Some of the compounds of the general formulae (VI) and (XV) are known or novel, in which case they can be prepared as described above.

The compounds of the general formulae (IX) and (X) are novel species and can be prepared as described above.

The compounds of the general formula (VIII) are novel and can be prepared by reacting compounds of the general formulae (XVa), (XVIII) and (XIX)

 (XVa)

(XVIII)

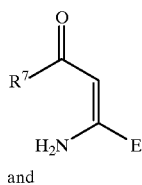

and (XIX)

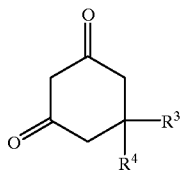

in which
A, E, $R^3$, $R^4$ and $R^7$ are as defined above,
with an acid.

Suitable solvents for preparing the compounds of the general formula (VIII) are the abovementioned ethers or alcohols. Preference is given to diisopropyl ether.

Suitable acids for preparing the compounds of the general formula (VIII) are, in general, organic carboxylic acids and inorganic acids, such as, for example, oxalic acid, maleic acid, phosphoric acid, fumatic acid and trifluoroacetic acid. Preference is given to trifluoroacetic acid and oxalic acid.

The acid is generally employed in an amount of from 0.1 mol to 5 mol, preferably 1 mol, based on 1 mol of the compounds of the general formula (XIX).

The reaction is generally carried out at atmospheric pressure. However, it is also possible to carry out the reaction under elevated or reduced pressure.

The reaction is generally carried out at the reflux temperature of the solvent in question.

The compounds of the general formulae (XV) and (XIX) are known per se or can be prepared by customary methods.

The compounds of the general formula (XVIII) are novel and can be prepared by first preparing, by reacting the compounds of the general formula (XX)

$$E-CO_2-R^{19} \qquad (XX)$$

in which

E is as defined above
and
$R^{19}$ represents $C_1-C_4$-alkyl with compounds of the general formula (XXI)

(XXI)

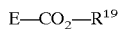

in which
$R^7$ is as defined above
in a solvent in the presence of 18-crown-6 ether, the compounds of the general formula (XXII)

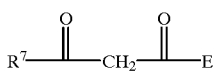

in which
$R^7$ and E are as defined above,
followed by reaction with ammonium acetate in inert solvents.

Suitable solvents for the first step of the process are the abovementioned ethers and hydrocarbons, and preference is given to tetrahydrofuran.

Suitable solvents for the reaction with the compounds of the general formula (XXII) are alcohols, such as, for example, methanol, ethanol, propanol or isopropanol. Preference is given to ethanol.

All steps of the process are carried out at the respective reflux temperature of the solvent in question and at atmospheric pressure.

Some of the compounds of the general formulae (XX) and (XXI) are known, or they can be prepared by known methods.

Some of the compounds of the general formula (XXII) are novel species, and they can be prepared as described above.

The compounds of the general formulae (I) and (Ia) according to the invention have a pharmacological activity spectrum which could not have been foreseen.

The compounds of the general formulae (I) and (Ia) according to the invention have useful pharmacological properties which are superior when compared to the prior art; in particular, they are highly effective inhibitors of cholesterol ester transfer protein (CETP) and they stimulate the reverse cholesterol transport. The active compounds according to the invention effect a reduction of the LDL cholesterol level in the blood and simultaneously increase the HDL cholesterol level. They can therefore be used for the treatment and prevention of hyperlipoproteinaemia, dyslipidaemias, hypertriglyceridaemias, hyperlipidaemias or arteriosclerosis.

The pharmacological activity of the substances according to the invention was assessed using the following test:
CETP Inhibition Test
Preparation of CETP CETP is obtained in partially purified form from human plasma by differential centrifugation and column chromatography and used for the test. For this purpose, human plasma is adjusted to a density of 1.21 g per ml using NaBr and centrifuged at 50,000 rpm at 4° C. for 18 h. The bottom fraction (d>1.21 g/ml) is applied to a Sephadex®Phenyl-Sepharose 4B (Pharmacia) column, washed with 0.15 m NaCl/0.001 M TrisHCl pH 7.4 and subsequently eluted using dist. water. The CETP-active fractions are pooled, dialysed against 50 mM Na-acetate pH 4.5 and applied to a CM-Sepharose® (Pharmacia) column. Elution is subsequently carried out using a linear gradient (0–1 M NaCl). The pooled CETP fractions are dialysed against 10 mM TrisHCl pH 7.4 and subsequently purified further by chromatography over a Mono Q® column (Pharmacia).

Preparation of radioactively labelled HDL 50 ml of fresh human EDTA plasma are adjusted to a density of 1.12 using NaBr and centrifuged at 4° C. in a Ty 65 rotor at 50,000 rpm for 18 h. The upper phase is used to obtain cold LDL. The lower phase is dialysed against 3*4 l of PDB buffer (10 mM Tris/HCl pH 7.4, 0.15 mM NaCl, 1 mM EDTA, 0.02% $NaN_3$). Per 10 ml volume of retained material, 20 ml of $^3$H-cholesterol (Dupont NET-725; 1 mC/ml, dissolved in ethanol) are subsequently added, and the mixture is incubated at 37° C. under $N_2$ for 72 h.

The mixture is then adjusted to a density of 1.21 using NaBr and centrifuged in a Ty 65 rotor at 20° C. and 50,000 rpm for 18 h. The upper phase is collected and the lipoprotein fractions are purified by gradient centrifugation. To this end, the isolated labelled lipoprotein fraction is adjusted to a density of 1.26 using NaBr. In each case 4 ml of this solution are covered in centrifuge tubes (SW 40 rotor) with 4 ml of a solution of a density of 1.21 and 4.5 ml of a solution of 1.063 (density solutions of PDB buffer and NaBr), and the tubes are subsequently centrifuged in an SW 40 rotor at 38,000 rpm and 20° C. for 24 h. The intermediate layer which is found between a density of 1.063 and a density of 1.21 and which contains the labelled HDL is dialysed against 3*100 volume of PDB buffer at 4° C.

The retained material contains radioactively labelled $^3$H-CE-HDL, which is used for the test adjusted to approximately $5 \times 10^6$ cmp per ml.

CETP Test

To assess the CETP activity, the transfer of $^3$H-cholesterol ester from human HD-lipoproteins to biotinylated LD-lipoproteins is measured.

The reaction is terminated by addition of Streptavidin-SPA® beads (Amersham) and the transferred radioactivity is directly measured in a liquid scintillation counter.

In the assay mixture, 10 ml of HDL-$^3$H-cholesterol ester (~50,000 cpm) with 10 ml of Biotin-LDL (Amersham) in 50 mM Hepes/0.15 m NaCl/0.1% bovine serum albumin/0.05% $NaN_3$ pH 7.4 are incubated with 10 ml of CETP (1 mg/ml) and 3 ml of a solution of the substance to be tested (dissolved in 10% DMSO/1% BSA) at 37° C. for 18 h. 200 ml of the SPA streptavidin bead solution (TRKQ 7005) are subsequently added, the mixture is incubated with shaking for another 1 h and subsequently measured in a scintillation counter.

The controls used are corresponding incubations with 10 ml of buffer, 10 ml of CETP at 4° C. and 10 ml of CETP at 37° C.

The activity which is transferrd in the control experiments with CETP at 37° C. is taken to be 100% transfer. The substance concentration at which this transfer is reduced by half is stated as the $IC_{50}$ value.

In Table A below, the $IC_{50}$ values (mol/l) for CETP inhibitors are given:

TABLE A

| Example No. | $IC_{50}$ value (mol/l) |
| --- | --- |
| 1 | $6 \times 10^{-9}$ |
| 53 | $1 \times 10^{-8}$ |
| 61 | $2.3 \times 10^{-8}$ |

Ex vivo Activity of the Compounds According to the Invention

Syrian gold hamsters, which have been bred in our own laboratory, are anaesthetized after 24 hours of fasting (0.8 mg/kg of atropine, 0.8 mg/kg of Ketavet® s.c., 30' later 50 mg/kg of nembutal i.p.). The jugular vein is subsequently exposed and cannulated. The test substance is dissolved in a suitable solvent (usually adalate placebo solution: 60 g of glycerol, 100 ml of $H_2O$, ad 1000 ml PEG-400) and administered to the animals via a PE catheter, which is introduced into the jugular vein. The same volume of solvent without test substance is administered to the control animals. The vein is subsequently tied off and the wound is closed The test substances can also be administered p.o. by dissolving the substances in DMSO and suspending them in 0.5% tylose and administering them perorally using a pharyngeal tube. Identical volumes of solvent without test substance are administered to the control animals.

At different intervals—up to 24 hours after the administration—blood samples are taken from the animals by puncture of the retro-orbital venous plexus (approximately 250 ml). Coagulation is completed by incubation at 4° C. overnight, and the samples are subsequently centrifuged at 6000xg for 10 minutes. The CETP activity is determined in the resulting serum using the modified CETP test. The transfer of $^3$H-holesterol ester from HD-lipoproteins to biotinylated LD-lipoproteins is measured as described above for the CETP test.

The reaction is terminated by addition of Streptavidin-SPA® beads (Amersham), and the transferred radioactivity is directly determined in a liquid scintillation counter.

The test protocol is carried out as described under "CETP test". However, to test the serun, 10 ml of CETP are replaced by 10 ml of the appropriate serum samples. Corresponding incubations of sera of untreated animals serve as controls.

The activity that is transferred in the control experiments using control sera is classified as 100% transfer. The substance concentration at which this transfer is reduced by half is stated as the $ED_{50}$ value In vivo Activity of the Compounds According to the Invention In experiments for assessing the oral activity on lipoproteins and triglycerides, test substance, dissolved in DMSO and suspended in 0.5% tylose, is administered perorally using a pharyngeal tube to Syrian gold hamsters which have been bred in our own laboratory. To determine the CETP activity, blood samples (approximately 250 ml) are taken by retro-orbital puncture prior to the start of the experiment. The test substances are subsequently administered perorally using a pharyngeal tube. Identical volumes of solvent without test substance are administered to the control animals. Subsequently, the animals have to fast and at different intervals—up to 24 hours after the administration of the substances—blood samples are taken by puncture of the retro-orbital venous plexus.

Coagulation is completed by incubation at 4° C. overnight, and the samples are subsequently centrifuged at 6000xg for 10 minutes. The content of cholesterol and triglycerides in the resulting serum is assessed using modified commercially available enzyme tests (cholesterol enzymatic 14366 Merck, triglycerides 14364 Merck). Serum is diluted in a suitable manner with physiological saline solution.

100 ml of serum dilution and 100 ml of test substance are transferred into 96-well-plates and incubated at room temperature for 10 minutes. The optical density is subsequently determined at a wavelength of 492 nm using an automatic plate reader. The triglyceride and cholesterol concentrations of the samples are determined with the aid of a standard curve measured in parallel.

The determination of the HDL-cholesterol content is carried out after precipitation of the ApoB-containing lipoproteins using a reagent mixture (Sigma 352-4 HDL cholesterol reagent) in accordance with the instructions of the manufacturer.

In vivo Activity in Transgenic hCETP Mice

The substances to be tested were administered to transgenic mice, which were bred in our own laboratory (Dinchuck, Hart, Gonzalez, Karmann, Schmidt, Wirak; BBA (1995), 1295, 301), via the feed. Prior to the beginning of the experiment, blood samples were taken retro-orbitally from the mice to determine cholesterol and triglycerides in the serum. The serum was obtained as described above for hamsters by incubation at 4° C. overnight and subsequent centrifugation at 6000×g. After one week, blood samples were again taken from the mice to determine lipoproteins and triglycerides. The change of the measured parameters are expressed as a change in per cent based on the initial value.

The invention furthermore relates to the combination of tetrahydroquinolenes of the general formula (I) with a glucosidase and/or amylase inhibitor for the treatment of familial hyperlipidaemias, of obesity (adipositas) and of diabetes mellitus. Glucosidase and/or amylase inhibitors in the context of the present invention are, for example, acarbose, adiposine, voglibose, miglitol, emiglitate, MDL-25637, camiglibose (MDL-73945), tendamistate, AI-3688, trestatin, pradimicin-Q and salbostatin.

Preference is given to the combination of acarbose, miglitol, emiglitate or voglibose with one of the abovementioned compounds of the general formula (I) according to the invention.

Furthermore, the compounds according to the invention can be combined with cholesterol-lowering vastatines or ApoB-lowering principles, in order to treat dyslipidaemias, combined hyperlipidaemias, hypercholesterolaemias or hypertriglyceridaemias.

The abovementioned combinations can also be used for primary or secondary prevention of coronary heart diseases (for example myocardial infarction).

Vastatins in the context of the present invention are, for example, lovastatin, simvastatin, pravastatin, fluvastatin, atorvastatin and cerivastatin. ApoB-lowering agents are, for example, MTP inhibitors.

Preference is given to the combination of cerivastatin or ApoB inhibitors with one of the abovementioned compounds of the general formula (I) according to the invention.

The novel active compounds can be converted in a known manner into the customary formulations, such as tablets, coated tablets, pills, granules, aerosols, syrups, emulsions, suspensions and solutions, using inert, non-toxic, pharmaceutically suitable carriers or solvents. In this case the therapeutically active compound should in each case be present in a concentration from approximately 0.5 to 90% by weight of the total mixture, i.e. in amounts which are sufficient in order to achieve the dosage range indicated.

The formulations are prepared, for example, by extending the active compounds using solvents and/or carriers, if appropriate using emulsifiers and/or dispersants, it optionally being possible, for example, to use organic solvents as auxiliary solvents if the diluent used is water.

Administration is carried out in a customary manner, intravenously, orally, parenterally or perlingually, in particular orally.

In the case of parenteral administration, solutions of the active compound can be used by employing suitable liquid carrier materials.

In general, it has proved advantageous, in the case of intravenous administration, to administer amounts from approximately 0.001 to 1 mg/kg, preferably approximately 0.01 to 0.5 mg/kg, of body weight to achieve effective results, and in the case of oral administration the dosage is approximately 0.01 to 20 mg/kg, preferably 0.1 to 10 mg/kg, of body weight In spite of this, if appropriate it may be necessary to depart from the amounts mentioned, namely depending on the body weight or on the type of administration route, on individual reaction towards the medicament, the manner of its formulation and the time at or interval during which administration takes place. Thus, in some cases it may be adequate to manage with less than the abovementioned minimum amounts, while in other cases the upper limit mentioned has to be exceeded. In the case of the administration of relatively large amounts, it may be advisable to divide these into several individual doses over the course of the day.

Abbreviations Used:

| Cy    | = | cyclohexane                    |
|-------|---|--------------------------------|
| EA    | = | ethyl acetate                  |
| PE    | = | petroleum ether                |
| THF   | = | tetrahydrofuran                |
| DAST  | = | dimethylaminosulphur trifluoride |
| PTA   | = | para-toluenesulphonic acid     |
| PDC   | = | pyridinium dichromate          |
| PE/EA | = | petroleum ether/ethyl acetate  |
| Tol   | = | toluene                        |

Starting Materials

EXAMPLE I

Methyl 2-cyclopentyl-4-(4-fluorophenyl)-5-oxo-7,7-dimethyl-1,4,5,6,7,8-hexahydroquinoline-3-carboxylate

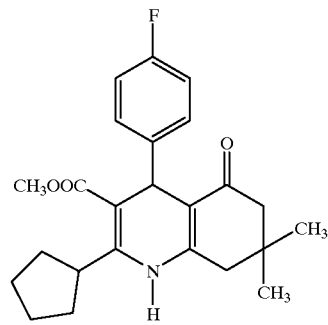

25.07 g (0.202 mol) of p-fluorobenzaldehyde, 28.32 g (0.202 mol) of 5,5-dimethyl-1,3-cyclohexanedione (dimedone) and 34.18 g (0.202 mol) of ethyl 3-amino-3-cyclopentylacrylate in 400 ml of ethanol are boiled under reflux for 24 hours. The mixture is cooled to room temperature and concentrated to dryness. The residue is suspended with heating in 180 ml of toluene and, during cooling, covered with a layer of petroleum ether, whereupon crystallization begins. The product which has crystallized out is filtered off with suction.

Yield: 41.21 g (51% of theory); TLC: $R_f$=0.07 (toluene/ethyl acetate=9:1).

EXAMPLE II

Methyl 2-cyclopentyl-4-(4-fluorophenyl)-5-oxo-7,7-dimethyl-5,6,7,8-tetrahydroquinoline-3-carboxylate

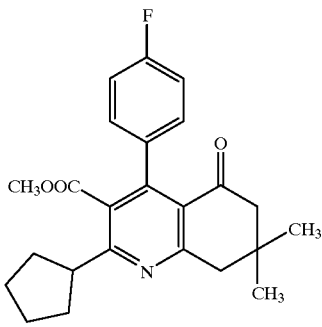

23.6 g (0.104 mol) of 2,3-dichloro-5,6-dicyano-p-benzioquinone (DDQ) are added to a solution of 41.2 g (0.104 mol) of the compound from Example I in 300 g of dichloromethan p.a., and the mixture is stirred at room temperature for 2 hours. The mixture is then filtered off with suction through 500 ml of silica gel 60 (0.04 to 0.063 mm), the silica gel is washed with 300 g of dichloromethane and the combined filtrates are concentrated to dryness. The crude product is eluted over silicagel using toluene in a gradient mode with ethyl acetate.

Yield: 38.31 g (94% of theory); TLC: $R_f$=0.6 (toluene/ethyl acetate 9:1).

EXAMPLE III

Methyl 2-cyclopentyl-4-(4-fluorphenyl)-5-hydroxy-7,7-dimethyl-5,6,7,8-tetrahydroquinoline-3carboxylate

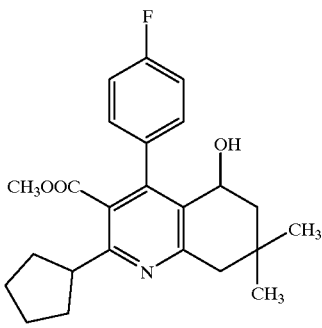

Under argon, 28 g (70.8 mmol) of the compound from Example II are dissolved in 700 ml of toluene p.a., the mixture is cooled to −78° C. and 84.96 ml (84.96 mmol; 1.2 eq.) of diusobutylaluminium hydride (DIBAL-H); 1.0 molar in toluene) are added dropwise over a period of 20 min. After 5 min of stirring at −78° C., the cooling bath is removed and the mixture is stirred for another 15 min. 500 ml of 20% strength potassium sodium tartrate solution are then added dropwise and the mixture is admixed with 600 ml of ethyl acetate. After 1 hour of stirring, the aqueous phase is separated off and reextracted twice with ethyl acetate, and the combined organic phases are dried over sodium sulphate, filtered and concentrated.

Yield: 27.66 g (98.2% of theory); TLC: $R_f$=0.37 (toluene/ethyl acetate, 9:1).

EXAMPLE IV

Methyl 5-(tertbutyldimethylsilanyloxy)-2-cyclopentyl-4-(4-fluorophenyl)-7,7-dimethyl-5,6,7,8-tetrahydroquinoline-3-carboxylate

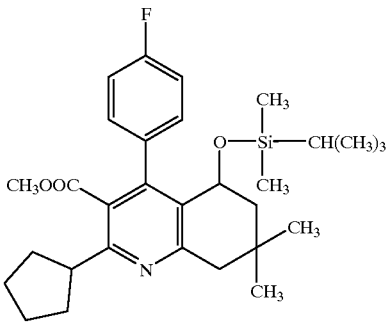

25.5 g (64.15 mmol) of the compound from Example III are dissolved in 300 g of methylene chloride and, under argon, admixed successively with 28.83 ml (0.2476 mol; 3.8 eq.) of 2,6-lutidine and 32.56 ml (0.1418 mol, 2.12 eq.) of tert.butyl-dimethylsilyl trifluoromethanesulphonate (TBS-triflate) at from −10° C. to 0° C. After 1 hour of stirring without cooling, the batch is stirred with 500 ml of ammonium chloride solution and 800 ml of ethyl acetate and adjusted to pH 5–6 using 6 molar hydrochloric acid. The organic phase is separated off, the aqueous phase is extracted two more times with ethyl acetate and the combined organic phases are dried over sodium sulphate, filtered and concentrated. The crude product is dissolved in toluene and chromatographed over silica gel using toluene.

Yield: 31.5 g (96% of theory); TLC: $R_f$=0.76 (toluene/ethyl acetate, 9:1).

EXAMPLE V 5-(tertButyldimethylsilanyloxy)-2-cyclopentyl-3-hydroxymethyl-4-(4-fluorophenyl)-7,7-dimethyl-5,6,7,8-tetrahydroquinoline

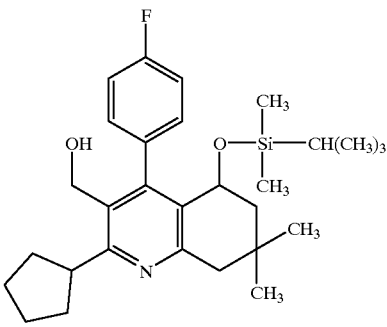

41.6 g (81.3 mmol) of the compound from Example IV are dissolved in 700 g of toluene p.a. and, under argon, cooled to −78° C. Over a period of 30–40 minutes, 244 ml (0.244 mol; 3 eq.) of DIBAL-H (1.0 molar in toluene) are added dropwise, and the mixture is subsequently stirred without cooling for 15 minutes. The reaction solution is stirred into 700 ml of 20% strength potassium sodium tartrate solution and covered with a layer of 350 ml of ethyl acetate. After 40 minutes of stirring, the organic phase is separated off and the aqueous phase is extracted twice with ethyl acetate. The combined organic phases are dried with $Na_2SO_4$, filtered, concentrated and dried under reduced pressure.

Yield: 39.42 g (100% of theory); TLC: $R_f$=0.54 (toluene/ethyl acetate, 9:1).

EXAMPLE VI 5-(tertButyidimethylsilanyloxy)-2-cyclopentyl)-4-(4-fluorophenyl)-7,7-dimethyl-5,6,7,8-tetrahydroquinoline-3-carbaldehyde

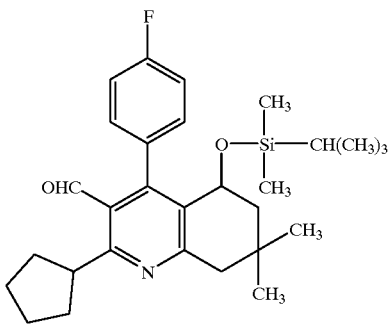

Under argon and at 0–5° C., 87 ml (1.23 mol, 1.5 eq.) of DMSO and 56.7 ml (0.407 mol, 5 eq.) of triethylamine are added to a solution of 39.4 g (81.5 mmol) of the compound from Example V in 400 ml of dichloromthane. 48.7 g (0.326 mol; 3.75 eq.) of sulphur trioxide-pyridine complex are then added, and the mixture is stirred for 2 hours with ice-cooling. The reaction solution is admixed with stirring with 250 mg of NaHCO$_3$ solution, the methylene chloride phase is separated off and the aqueous phase is washed twice with methylene chloride. The combined organic phases dried over Na$_2$SO$_4$ and concentrated. The residue—dissolved in toluene—is chromatographed over silica gel using toluo, toluene/ethyl acetate.

Yield: 32.61 g (83% of theory); TLC: R$_f$=0.92 (toluene/ethyl acetate, 9:1).

EXAMPLE VII 5-(tertButyldimethylsilanyloxy)-2-cyclopentyl-4-(4-fluorophenyl)-3-[hydroxy-(4-trifluoromethylphenyl)-methyl]-7,7-dimethyl-5,6,7,8-tetrahydroquinoline

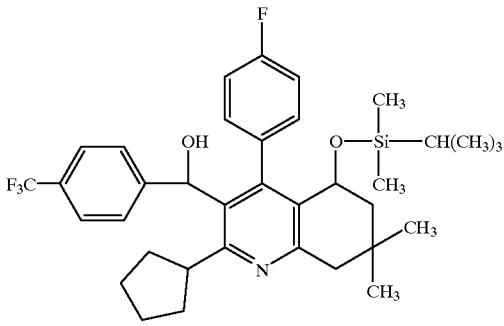

5.50 g (0.2262 mol, 6 eq.) of magnesium turnings are initially charged in 230 g of THF p.a., the mixture is, under argon, heated to reflux and 7.92 ml (0.05655 mol; 1.5 eq.) of 4-bromobenzotrifluoride are added dropwise using a syringe. The mixture is boiled under reflux for 60 min and then allowed to cool to room temperature (Grignard reagent). 18.17 g (0.0377 mol) of the compound from Example VI are dissolved in 115 g of THF p.a. and, under argon, cooled to approximately −78° C., and the Grignard reagent is added with stirring. The cooling bath is removed and the batch is stirred for 1 hour. The reaction solution is partitioned wth stirring in 600 ml of conc. ammonium chloride solution and 500 ml of ethyl acetate, the organic phases are separated off, the aqueous phase is extracted once more with ethyl acetate and the combined organic layers are dried with sodium sulphate, filtered, concentrated and dried under high vacuum. The two diastereomers (Dia A and Dia B) are separated by chromatography over 1 kg of silica gel—conditioned with cyclohexane, by eluting the crude product in 60 ml of cyclohexane/THF (9:1). Concentration of the fractions gives the 2 pairs of diastereomers:

Yields:

Dia A:
    18.5 g (78.2% of theory);
    TLC: R$_f$=0.54 (cyclohexane/THF, 9:1);

Dia B:
    6.3 g (26.6% of theory);
    TLC: R$_f$=0.41 (cyclohexane/THF, 9:1).

EXAMPLE VIII 5-(tertButyidimethylsilanyloxy)-2-cyclopentyl-4(4-fluorophenyl)-3-[fluoro-(4-trifluoromethyl)-methyl]-7,7-dimethyl-5,6,7,8tetrahydroquinoline (Dia A)

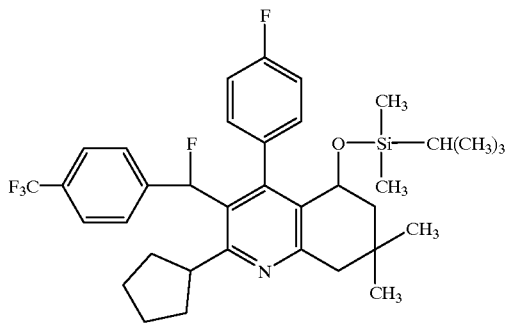

At −78° C. and under argon, 1.042 ml (7.88 mmol, 1.5 eq.) of diethylaminosulphur trifluoride (DAST) are added with a syringe to a solution of 3.3 g (5.26 mmol) of the compound Dia A from Example VII in 150 ml of dichloromethane p.a., and the cooling bath is then removed and the mixture is stirred for 30 minutes. The reaction solution is subsequently stirred into ethyl acetate/ammonium chloride solution, the organic phase is separated off, the aqueous phase is extracted three times with ethyl acetate, and the combined organic extract is dried with Na$_2$SO$_4$, filtered, concentrated and dried under high vacuum.

Yield: 3.1 g (93.7% of theory); TLC: R$_f$=0.79 (toluene/ethyl acetate=9:1).

EXAMPLE IX 5-(tertButyidimethylsilanyloxy)-2-cyclopentyl-4-(4-fluorophenyl)-3-[fluoro-(4-trifluoromethyl)methyl]-7,7-dimethyl-5,6,7,8-tetrahydroquinoline (Dia B)

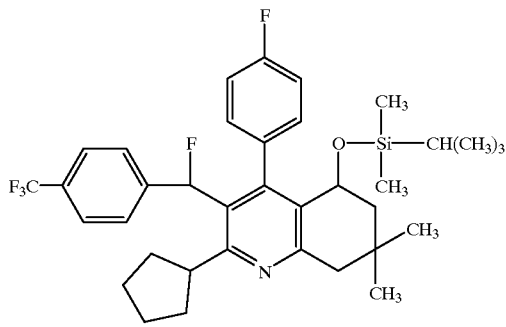

Analogously to Example VIII, 6.3 g (10 mmol) of the compound Dia B from Example VI in 200 g of dichloromethane p.a. are reacted with 2.0 ml (15 mmol; 1.5 eq.) of DAST at −78° C.

Yield: 5.9 g (93.6% of theory); TLC: $R_f$=0.75 (cyclohexane/THF 9:1).

EXAMPLE X

2-Cyclopentyl-4-(4-fluorophenyl)-3-[fluoro-(4-trifluoromethyl-phenyl)-methyl]-7,7-dimethyl-5,6,7,8-tetrahydroquinolin-5-ol (Dia A)

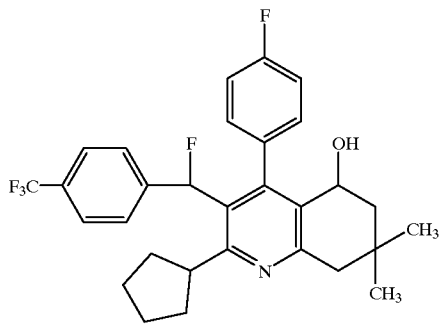

60 ml of 6 molar hydrochloric acid are added to 3.1 g (4.92 mmol) of the compound from Example VIII—dissolved in 200 ml of methanol and 46 ml of THF—and the mixture is stirred at 60° C. for 1.5 hours. The reaction solution is stirred into saturated sodium bicarbonate solution which is covered with a layer of ethyl acetate. The organic phase is separated off and the aqueous phase is extracted twice with ethyl acetate. The combined organic phases are washed once with saturated sodium chloride solution, dried over $Na_sSO_4$, filtered and concentrated. The residue is chromatographed over 150 ml of silica gel 60 one another with toluene and toluene/ethyl acetate (8:2).

Yield: 2.43 g (95.7% of theory); TLC: $R_f$=0.61 (toluene/ethyl acetate, 9:1).

EXAMPLE XI

2-Cyclopentyl-4-(4-fluorophenyl)-3-[fluoro-(4-trifluoromethyl-phenyl)-methyl]-5-oxo-7,7-dimethyl-5,6,7,8-tetrahydroquinoline

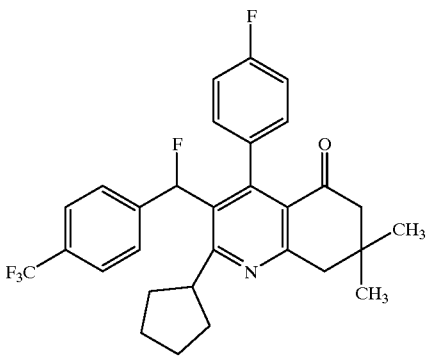

At room temperature, 3.0 g (5.819 mmol) of the compound enantiomer I from 2-cyclopentyl-4-(4-fluorophenyl)-3-[fluoro-(4-trifluoromethyl-phenyl)-methyl]-7,7-dimethyl-5,6,7,8-tetrahydroquinolin-5-ol in 270 ml of dichloromethane p.a. are reacted with 6.57 g (17.452 mmol; 3 eq.) of pyridinium dichromate. After 5 hours, the reaction solution is applied to 300 ml of silica gel which had been conditioned with dichloromethane beforehand, and the solution is eluted with dichloromethane. The fractions containing the pure product are combined and concentrated.

Yield. 2.64 g; TLC: $R_f$=0.66 (toluene/ethyl acetate, 9:1).

PREPARATION EXAMPLES

Example 1 and 2

2-Cyclopentyl-4-(4-fluorophenyl)-3-[fluoro-(4-trifluoromethyl-phenyl)-methyl]-5-methyl-7,7-dimethyl-5,6,7,8-tetrahydro-quinolin-5-ol

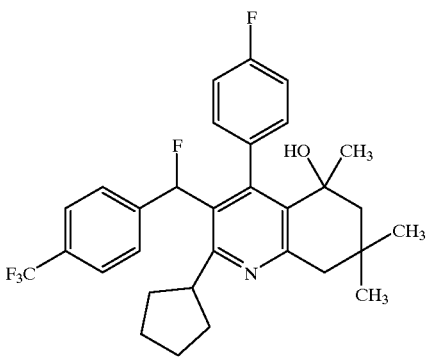

514 mg (1 mmol) of the keto compound from Example XI are dissolved in 50 ml of ether p.a. (which had been dried over a molecular sieve), and the mixture is cooled under argon to −78° C. and admixed dropwise with 3.1 ml (5 mmol, 5 eq.) of methyllithium (1.6 molar solution in ether). The solution is subsequently stored at −30° C. (deep freezer) for 20 hours. The solution is then cooled to −78° C. and admixed with 20 ml of ammonium chloride solution and 40 ml of toluene p.a. The cooling bath is removed and the solution is allowed to warm to room temperature. The organic phase is separated off, the aqueous phase is extracted twice with toluene and the combined organic phases are dried over $Na_2SO_4$, filtered and concentrated. The residue—dissolved in toluene—is chromatographed over 500 ml of silica gel using cyclohexane with a little added ethyl acetate as eluent.

Example 1
Isomer A:
 Yield: 39 mg;
 TLC: $R_f$=0.57 (dichloromethane).

Example 2
Isomer B:
 Yield: 39 mg;
 TLC: $R_f$=0.48 (dichloromethane).

Example 3
[2-Cyclopentyl-4-(3,4-difluorophenyl)-5-hydroxy-7,7-dimethyl-5,6,7,8-tetrahydroquinolin-3-yl]-(4trifluoromethylphenyl)methanone

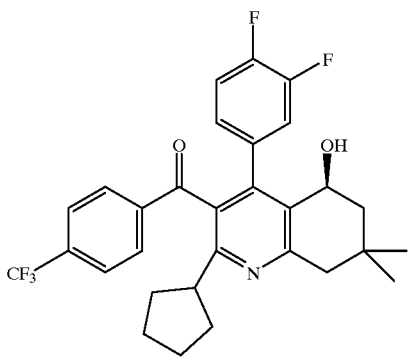

a) 2-Cyclopentyl4-(3,4-difluorophenyl)-7,7dimethyl-3-(4-trifluoromethylbenzoyl)-7,8-dihydro-6H-quinolin-5-one

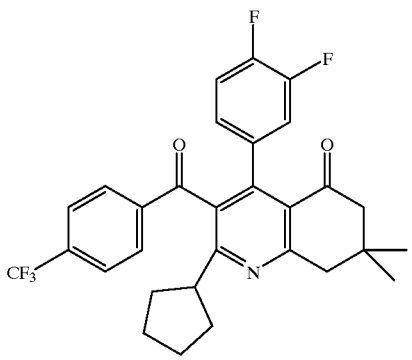

0.9 g (1.7 mmol) of 2-cyclopentyl-4-(3,4-difluorophenyl)-7,7-dimethyl-3-(4-trifluoromethylbenzoyl)-4,6,7,8-tetrahydro-1H-quinolin-5-one were oxidized at room temperature within one hour to give the pyridine, using 4.5 g of manganese dioxide (activated) in 25 ml of methylene chloride. The manganese dioxide was separated off and the methylene chloride was distilled off, and the mixture was then filtered off with suction using petroleum ether. This gave 0.8 g of crystals of melting, point: 210–212° C.

b) 2.1 g (4 mmol) of 2-cyclopentyl-4-(3,4-difluorophenyl)-7,7-dimethyl-3-(4-trifluoromethylbenzoyl)-7,8-dihydro-6H-quinolin-5-one were dissolved in 20 ml of tetrahydrofumn and, at 0° C., added dropwise to a solution of 0.2 g (1.2 mmol) of 1R,2S-aminoindanol and 2.7 ml (16 mmol) of boranediethylaniline complex in 2 ml of THF. The mixture is stirred at RT overnight. After about 20 hours, the reaction was quenched using 2.4 ml of 1,2-ethanediol.

The tetrahydrofuran was distilled off, the resulting oil was taken up in ethyl acetate and the organic phase was, after washing with 2N hydrochloric acid and saturated sodium bicarbonate solution, dried and concentrated. The residue was recrystallized from hot cyclohexane. This gave a total of 1.4 g of colourless crystals of melting point: 166–168° C.

Example 4
2-Cyclopentyl-4-(3,4-difluorophenyl)-3-[fluoro-(4-tlifluoromethylphenyl)-methyl]-7,7-dimethyl-5,6,7,8-tetrahydroquinolin-5-ol

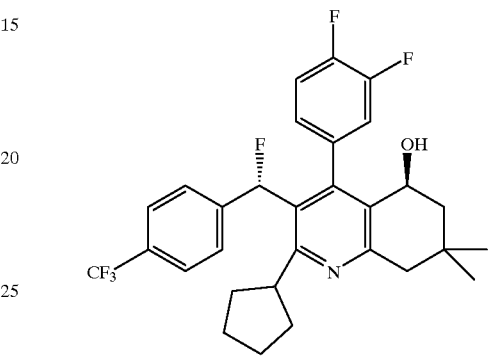

a) [5-(tert-Butyidimethylsilanyloxy)-2-cyclopentyl-4-(3,4-difluorophenyl)-7,7-dimethyl-5,6,7,8-tetrahydroquinolin-3-yl]-(4-trifluoromethylpbenyl)-methanone

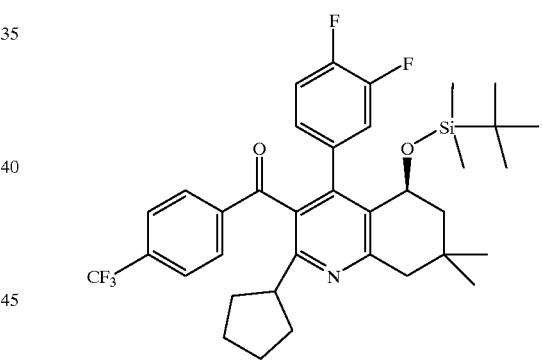

0.529 g (1 mmol) of [2-cyclopentyl-4-(3,4-difluorophenyl)-5-hydroxy-7,7-dimethyl-5,6,7,8-tetrahydro-quinolin-3-yl]-(4-trifluoromethylphenyl)-methanone are dissolved in 6 ml of abs. toluene and admixed with 0.465 ml of lutidine at −5° C. At from −5° C. to −10° C., 0.459 ml (2 mmol) of tert-butyldimethylsilyl trifluoromethanesulphonate is added. The mixture is stirred at 20° C. for 3 hours. The mixture is diluted with toluene, the reaction is quenched with 10% strength aqueous ammonium chloride solution and the organic phase is washed with 0.1 N hydrochloric acid and saturated aqueous sodium bicarbonate solution and dried. The solvent is distilled off under reduced pressure and the residue is then purified using a column. This gives 620 mg of colourless crystals of melting point: 128° C.–129° C.

b) [5-(tert-Butyldimethylsilanyloxy)-2-cyclopentyl-4-(3,4-difluorophenyl)-7,7-dimethyl-5,6,7,8-tetrahydroquinolin-3-yl]-(4-tiifluoromethylphenyl)-methanol

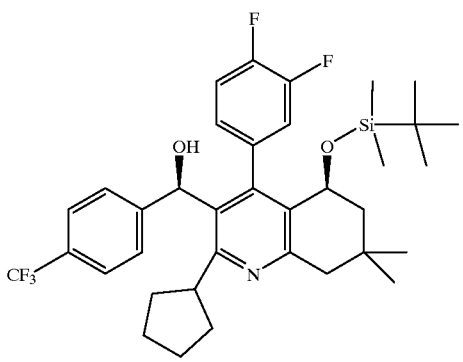

At 0° C., 1.15 ml (4 mmol) of sodium bis-(2-methoxyethoxy)-aluminium dihydride (65% strength in toluene) were added dropwise to 600 mg (0.93 mmol) of [5-(tert-butyldimethylsilanyloxy)-2-cyclopentyl-4-(3,4-difluorophenyl)-7,7-dimethyl-5,6,7,8-tetrahydroquinolin-3-yl]-(4-trifluoromethylphenyl)-methanone dissolved in 6 ml of toluene. After 3.5 hours, the reaction was quenched with methanol, the mixture was extracted with ethyl acetate and the organic phase was washed with potassium-sodium tartrate solution and saturated aqueous sodium bicarbonate solution and dried. The solvent is distilled off under reduced pressure and the residue is then purified over a silica gel column using toluene/ethyl acetate. This gives a total of 0.56 g of a colourless foam.

c) 5-(tert-Butyldimethylsilanyloxy)-2-cyclopentyl-4-(3,4-difluorophenyl)-3-[fluoro-(4-trifluoromethylphenyl)-methyl]-7,7-dimethyl-5,6,7,8-tetrahydroquinoline

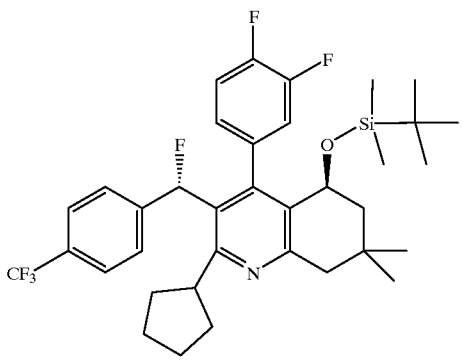

At −5° C., 0.06 ml of diethylaminosulphur trifluoride, dissolved in 10.15 ml of toluene, was added dropwise to 200 mg (0.3 mmol) of [5-(tertbutyldimethylsilanyloxy)-2-cyclopentyl-4-(3,4-difluorophenyl)-7,7-dimethyl-5,6,7,8-tetrahydroquinolin-3-yl]-(4-trifluoromethylphenyl)-methanol dissolved in 2 ml of toluene. After 60 minutes, the reaction was quenched with saturated aqueous sodium bicarbonate solution, toluene was added and the organic phase was washed once more with saturated aqueous sodium bicarbonate solution and dried. The solvent was distilled off under reduced pressure and the residue was then purified over a silica gel column This gave a total of 190 mg of a colourless oil.

d) 190 mg of 5-(tert-butyldimethylsilanyloxy)-2-cyclopentyl-4-(3,4-difluorophenyl)-3-[fluoro-(4-trifluoromethylphenyl)methyl]-7,7-dimethyl-5,6,7,8-tetrahydroquinoline, in a mixture of 1.6 mL of 5 N hydrochloric acid, 2.3 ml of methanol and 1.5 ml of tetrahydrofuran, were stirred at RT for 1 hour and then at 40° C.–45° C. for 2 hours. Some of the compound precipitated out as a by-product. This gives 80 mg of m.p. 206–207° C. The mother liquor is admixed with saturated aqueous sodium bicarbonate solution and with ethyl acetate. The organic phase is once more washed with saturated aqueous sodium bicarbonate solution and then dried. The solvent is distilled off under reduced pressure and the residue is then purified over a silica gel column. Crystallization with beptane gives 40 mg of the base of m.p. 149–150° C.

Example 5

2-Cyclopropyl-4-(3,4-difluorophenyl)-3-(4-trifluoromethylbenzyl)-7,7dimethyl-5,6,7,8-tetrahydroquinolin-5-ol

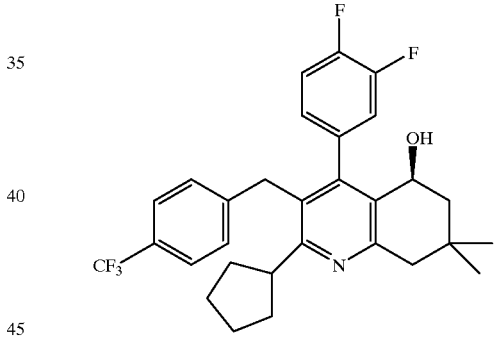

280 mg (0.52 mmol) of the compound from Example 4 are dissolved in 40 ml of abs. toluene and, at from −10° C. to −15° C., admixed dropwise with 3.5 ml of 25% strength diisobutylaluminium hyride solution. The mixture is stirred for 1 hour, cooled to −70° C. and admixed dropwise with 0.2 ml of methanol. At 20° C., the mixture is admixed with sodium chloride solution, the phases are separated and the organic phase is dried. The evaporation residue is purified over a silica gel column Crystallization from heptane gives 195 mg of colourless crystals of mp. 126–127° C.

The compounds listed in Table 1 are prepared analogously to the procedure of Examples 1 to 5:

TABLE 1

| Example No. | Structure | Isomer | R_f value/m.p. (° C.) |
|---|---|---|---|
| 6 | 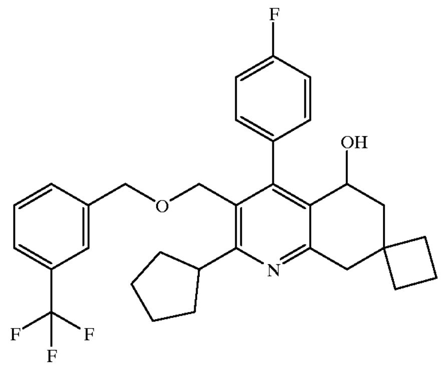 | racemate | 0.50<br>toluene/EA<br>(9:1) |
| 7 | 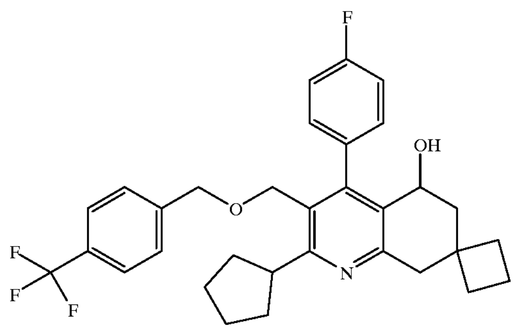 | racemate | Lichrosorb Si 60: 2.785<br>n-heptane/ethanol<br>(95:5) |
| 8 | 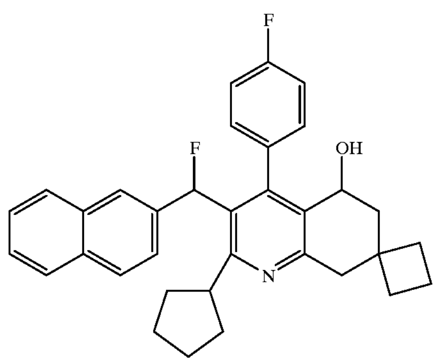 | diastereomer A | 0.32<br>cyclohexane/EA<br>(9:1) |
| 9 | 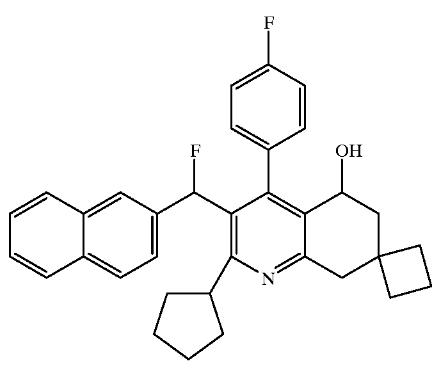 | diastereomer B | 0.58<br>toluene/EA<br>(9:1) |

TABLE 1-continued

| Example No. | Structure | Isomer | R_f value/m.p. (° C.) |
|---|---|---|---|
| 10 | 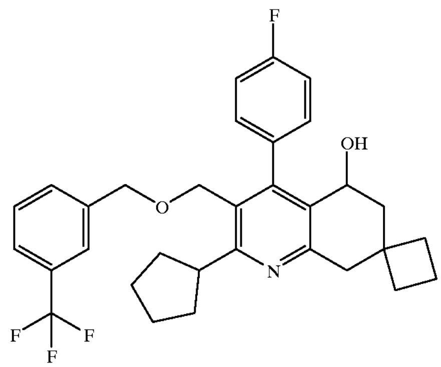 | enantiomer II | Chiral AD: 79.551<br>n-heptane/2-propanol<br>(99:1) |
| 11 | 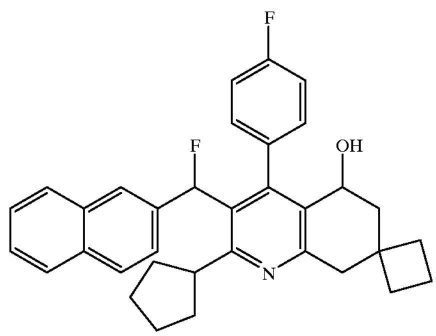 | enantiomer I | 0.2<br>cyclohexane/EA<br>(9:1) |
| 12 | 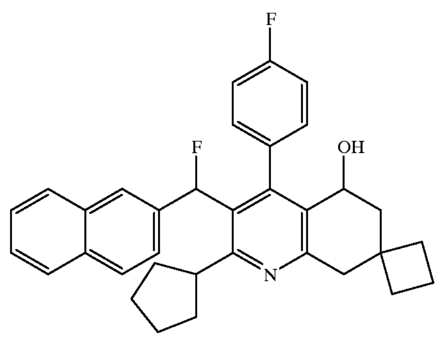 | enantiomer II | KBD 4922C column: 9.50<br>(Bayer AG)<br>n-heptane/THF<br>(100:3) |
| 13 | 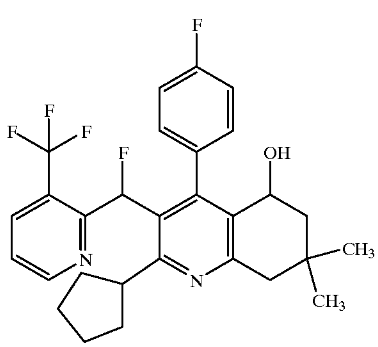 | diastereomer A | 0.73<br>toluene/EA<br>(8:2) |

TABLE 1-continued

| Example No. | Structure | Isomer | R_f value/m.p. (° C.) |
|---|---|---|---|
| 14 | 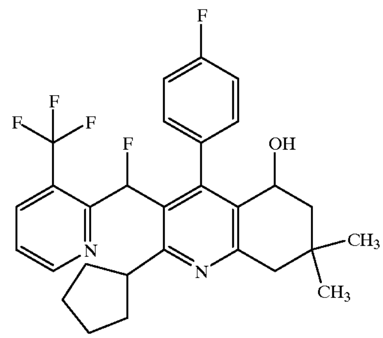 | diastereomer B | 0.16 cyclohexane/EA (8:2) |
| 15 | 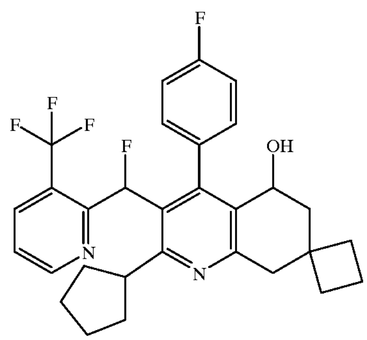 | diastereomer B | 0.50 toluene/EA (8:2) |
| 16 | 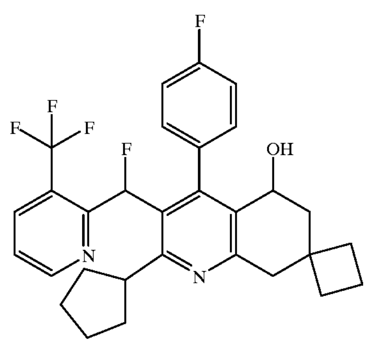 | diastereomer A | 0.40 cyclohexane/EA (8:2) |
| 17 | 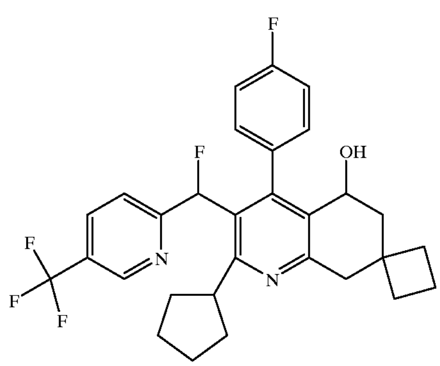 | diastereomer A | 0.55 toluene/EA (9:1) |

TABLE 1-continued

| Example No. | Structure | Isomer | R_f value/m.p. (° C.) |
|---|---|---|---|
| 18 | 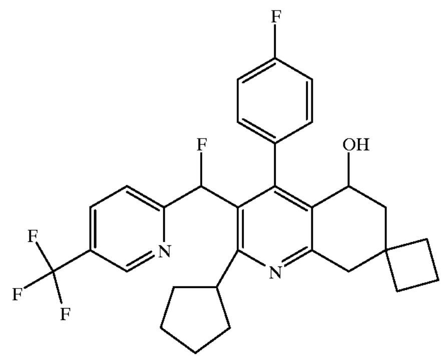 | diastereomer B | 0.48 toluene/EA (9:1) |
| 19 | 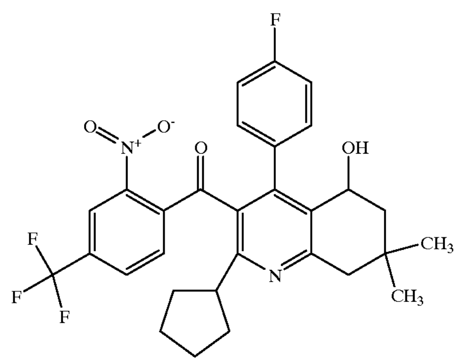 | racemate | 0.34 toluene/EA (95:5) |
| 20 | 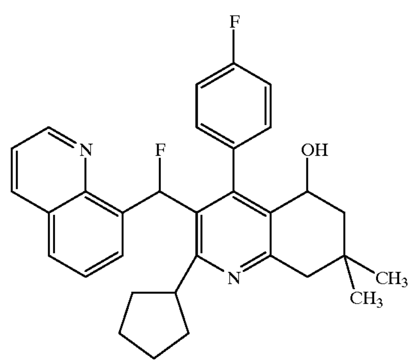 | diastereomer B | 0.53 toluene/EA (9:1) |
| 21 | 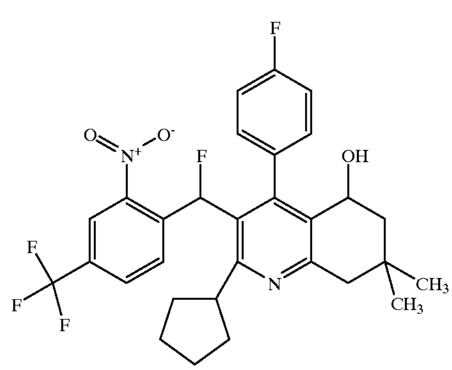 | diastereomer A, B | 0.43 and 0.46 toluene/EA (95:5) |

TABLE 1-continued

| Example No. | Structure | Isomer | R_f value/m.p. (° C.) |
|---|---|---|---|
| 22 | 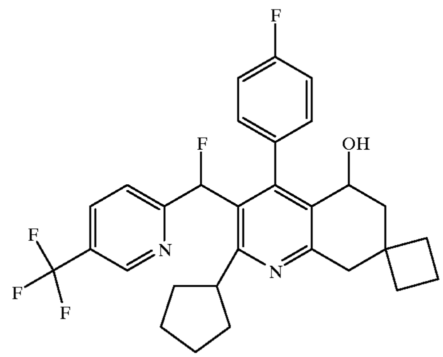 | enantiomer I | KBD 4922 C column: 4.82 (Bayer AG) n-heptane/THF (9:1) |
| 23 | 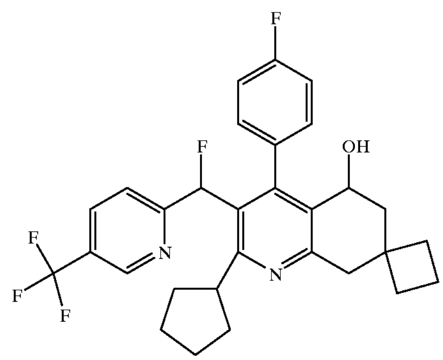 | enantiomer II | KBD 4922 C column: 7.32 (Bayer AG) n-heptane/THF (9:1) |
| 24 | 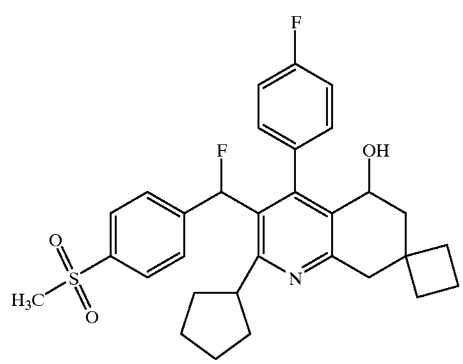 | | 0.41 toluene/EA (95:5) |
| 25 | 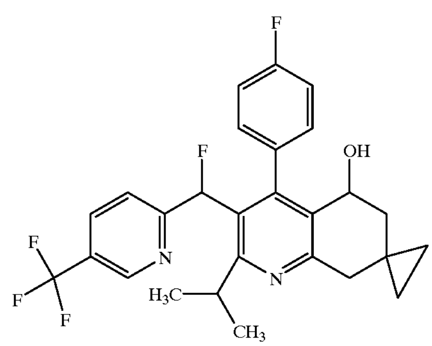 | diastereomer A | 0.16 toluene/EA (95:5) |

TABLE 1-continued

| Example No. | Structure | Isomer | $R_f$ value/m.p. (° C.) |
|---|---|---|---|
| 26 | 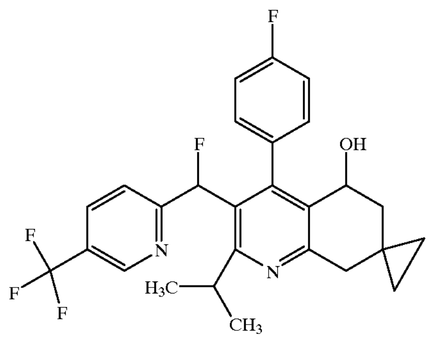 | diastereomer B | 0.66 toluene/EA (9:1) |
| 27 | 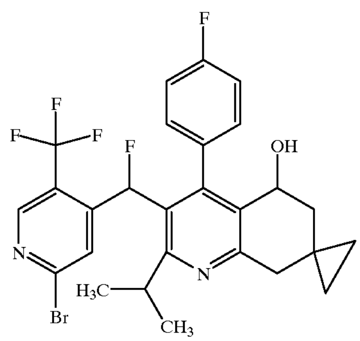 | | 0.22 toluene/EA (9:1) |
| 28 | 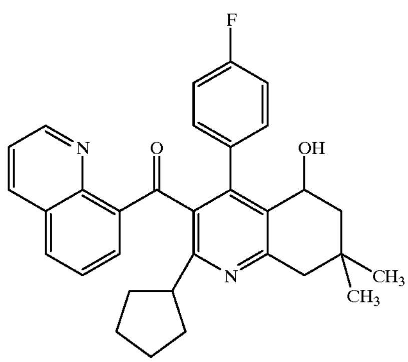 | diastereomer A | 0.44 toluene/EA (9:1) |
| 29 | 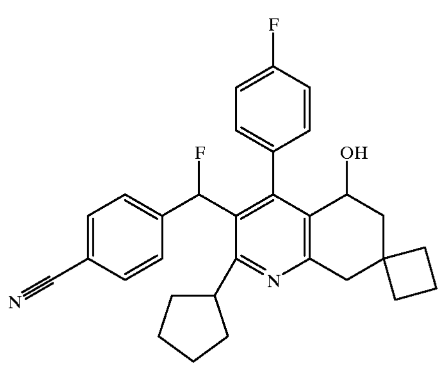 | diastereomer A | 0.36 toluene/EA (95:5) |

TABLE 1-continued

| Example No. | Structure | Isomer | $R_f$ value/m.p. (° C.) |
|---|---|---|---|
| 30 | 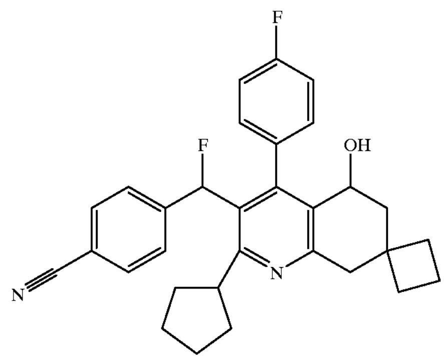 | diastereomer B | 0.37 toluene/EA (95:5) |
| 31 | 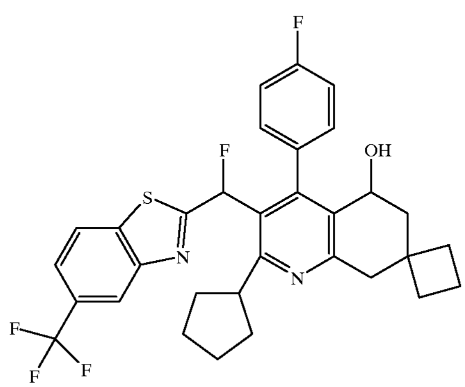 | diastereomer A | 0.48 toluene/EA (95:5) |
| 32 | 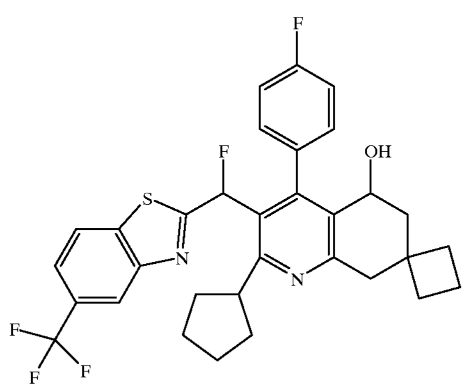 | diastereomer B | 0.45 toluene/EA (95:5) |
| 33 | 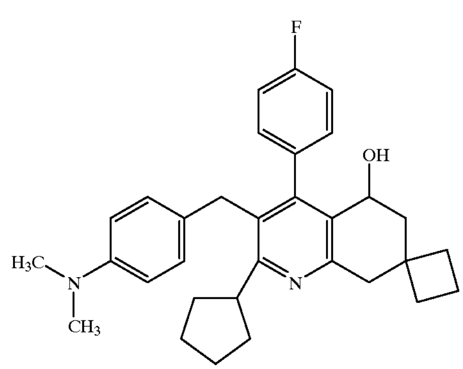 | racemate | 0.42 toluene/EA (9:1) |

TABLE 1-continued
| Example No. | Structure | Isomer | $R_f$ value/m.p. (° C.) |
|---|---|---|---|
| 34 | 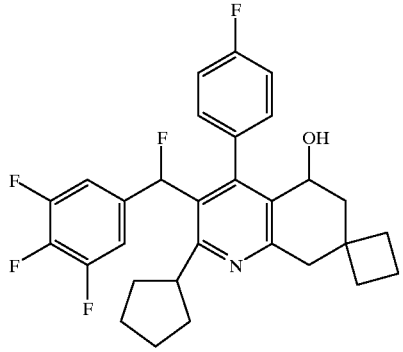 | diastereomer B | 0.65 toluene/EA (9:1) |
| 35 | 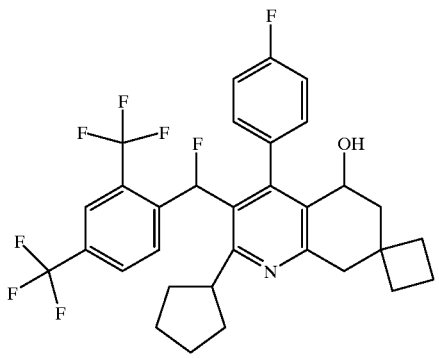 | diastereomer A | 0.47 toluene/EA (95:5) |
| 36 | 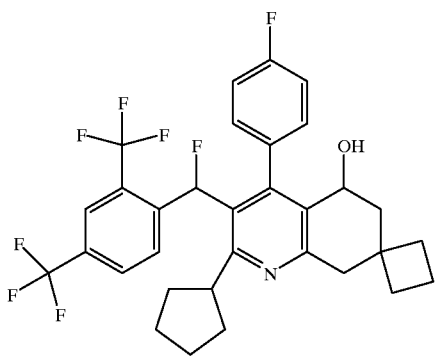 | diastereomer B | 0.45 toluene/EA (95:5) |
| 37 | 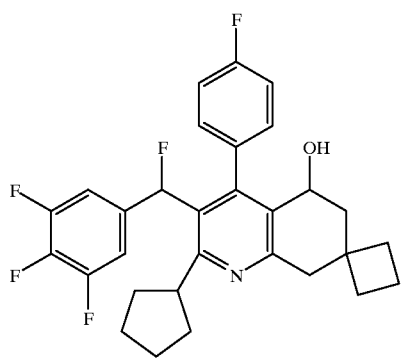 | diastereomer A | 0.61 toluene/EA (9:1) |

TABLE 1-continued
| Example No. | Structure | Isomer | $R_f$ value/m.p. (° C.) |
| --- | --- | --- | --- |
| 38 | 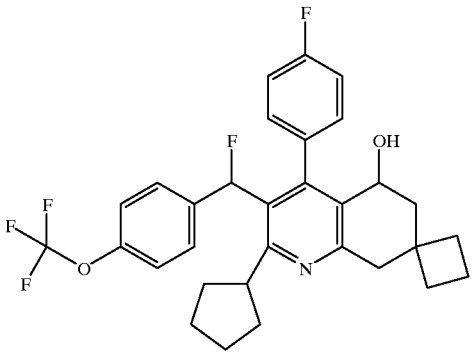 | diastereomer A | 0.33 toluene/EA (9:1) |
| 39 | 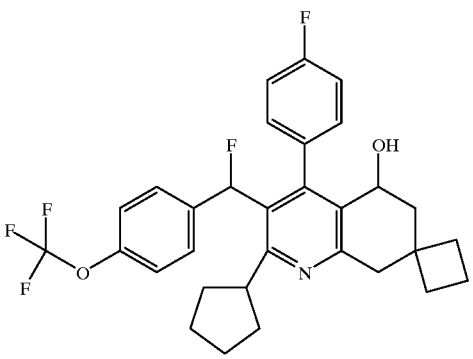 | diastereomer B | 0.32 toluene/EA (9:1) |
| 40 | 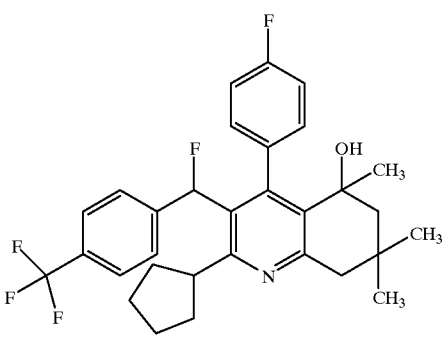 | diastereomer A | 0.57 dichloromethane |
| 41 | 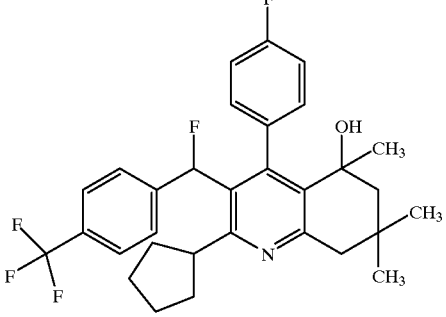 | diastereomer B | 0.48 dichloromethane |

TABLE 1-continued

| Example No. | Structure | Isomer | R_f value/m.p. (° C.) |
|---|---|---|---|
| 42 | 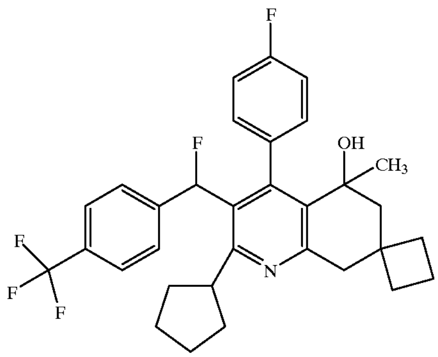 | diastereomer A | 0.51 cyclohexane/EA (8:2) |
| 43 | 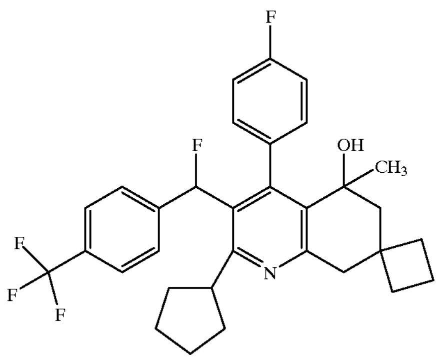 | diastereomer B | 0.44 cyclohexane/EA (8:2) |
| 44 | 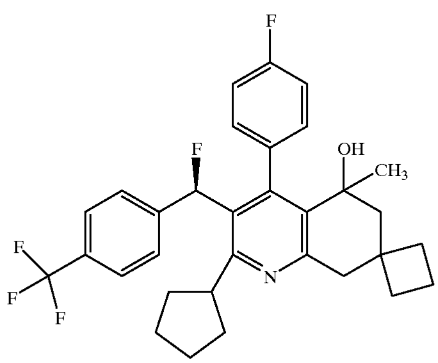 | diastereomer A | 0.52 methylene chloride |
| 45 | 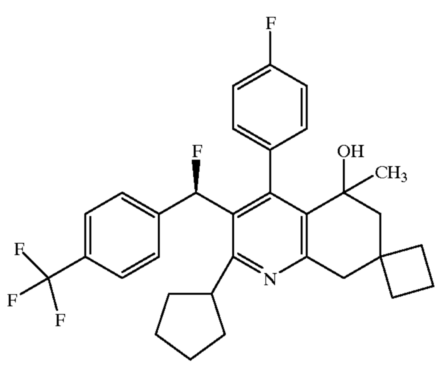 | diastereomer B | 0.41 methylene chloride |

TABLE 1-continued

| Example No. | Structure | Isomer | R_f value/m.p. (° C.) |
|---|---|---|---|
| 46 | 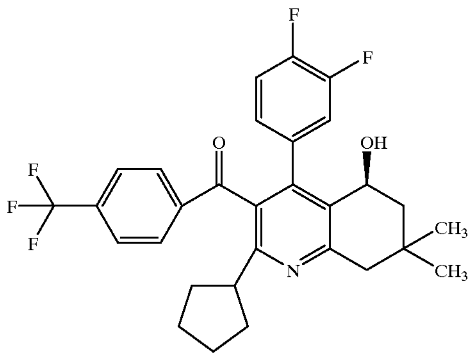 | | m.p.: 166–168° C. |
| 47 | 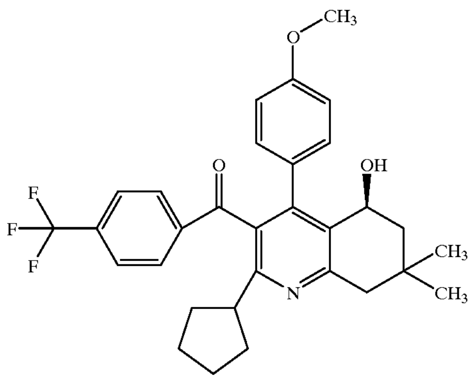 | | m.p.: 171–174° C. |
| 48 | 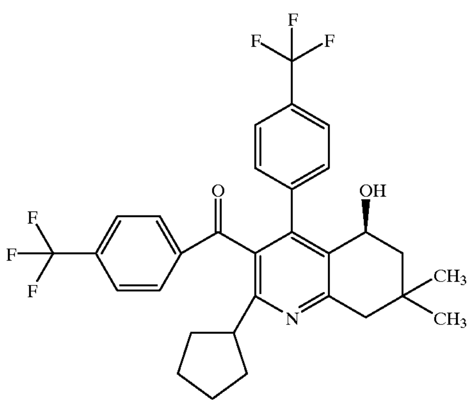 | | m.p.: 157–162° C. |
| 49 | 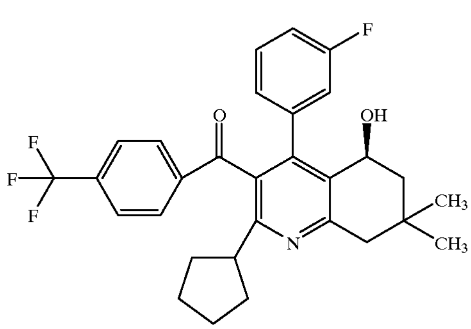 | | m.p.: 167–168° C. |

TABLE 1-continued

| Example No. | Structure | Isomer | $R_f$ value/m.p. (° C.) |
|---|---|---|---|
| 50 | 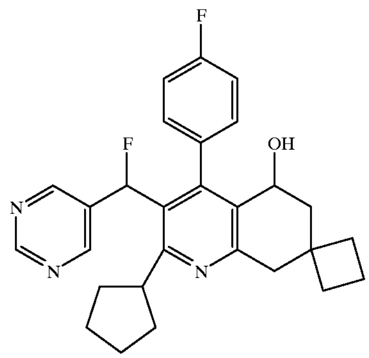 | diastereomer B | 0.33 toluene/EA (7:3) |
| 51 | 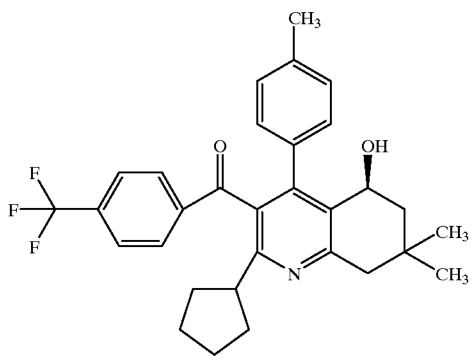 | | m.p.: 153–155° C. |
| 52 | 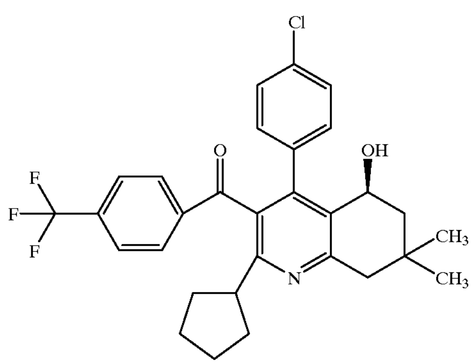 | | m.p.: 168–169° C. |
| 53 | 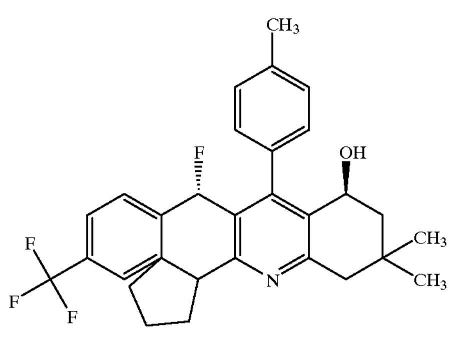 | | m.p.: 156–158° C. |

TABLE 1-continued

| Example No. | Structure | Isomer | R$_f$ value/m.p. (° C.) |
| --- | --- | --- | --- |
| 54 | 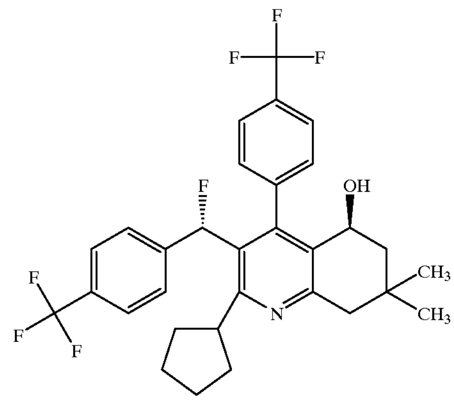 | | m.p.: 175–176° C. |
| 55 | 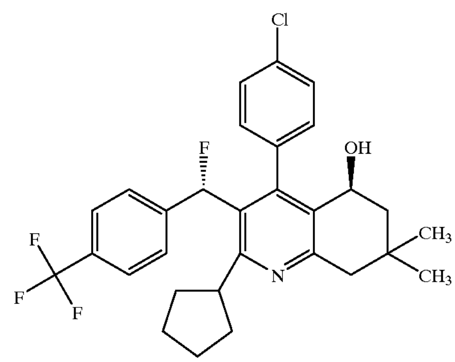 | | m.p.: 138–139° C. |
| 56 | 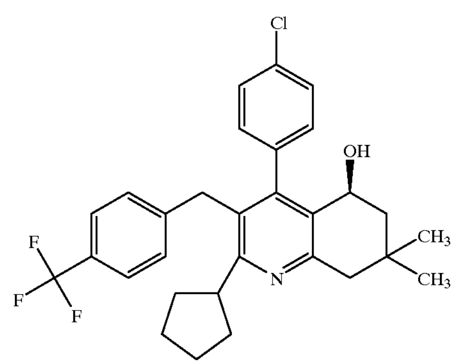 | | m.p.: 136–137° C. |
| 57 | 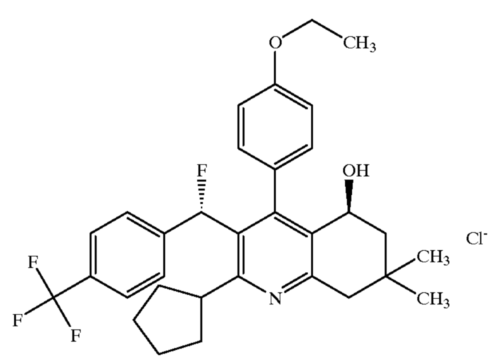 | | m.p.: 206–207° C. |

TABLE 1-continued

| Example No. | Structure | Isomer | R_f value/m.p. (° C.) |
|---|---|---|---|
| 58 | 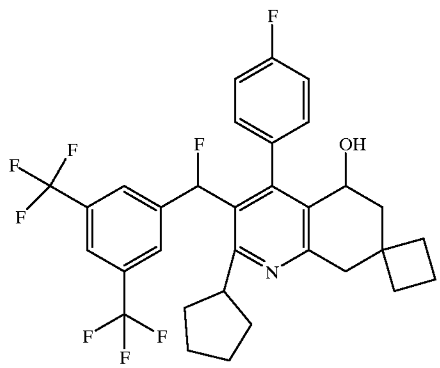 | mixture of diastereomers | 0.62 toluene/EA (9:1) |
| 59 | 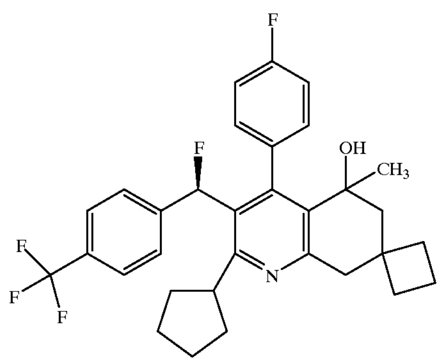 | diastereomer A | 0.52 methylene chloride |
| 60 | 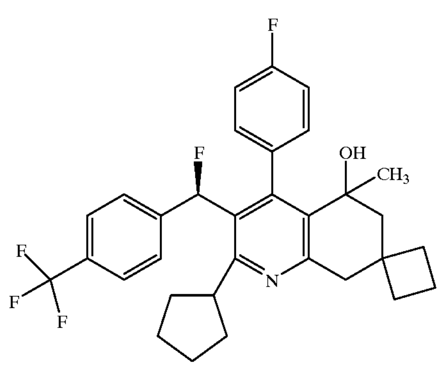 | diastereomer B | 0.41 methylene chloride |
| 61 | 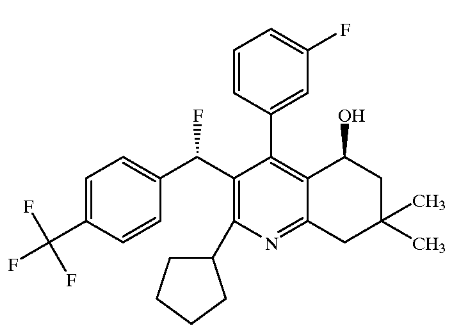 | atropisomer | m.p.: 129° C. (from 129° C.) |

TABLE 1-continued

| Example No. | Structure | Isomer | $R_f$ value/m.p. (° C.) |
|---|---|---|---|
| 62 | 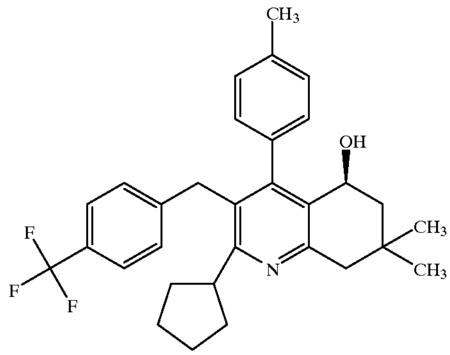 | | m.p.: 106–108° C. |
| 63 | 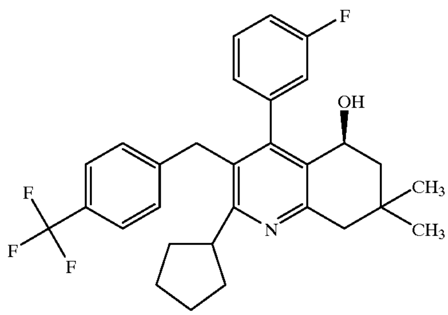 | atropisomer | 0.19 and 0.39 petroleum ether/EA (10:1) |
| 64 | 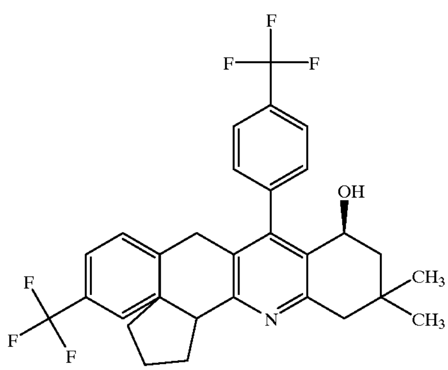 | | 0.37 toluene/EA (20:1) |

What is claimed is:

1. A tetrahydroquinoline of the formula (I):

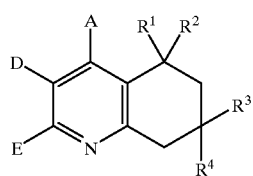

(I)

in which

A represents phenyl which is optionally substituted 1 to 2 times by identical or different substituents selected from the group consisting of halogen, trifluoromethyl and straight-chain or branched alkyl or alkoxy having in each case 1 to 3 carbon atoms;

D represents a radical of the formula:

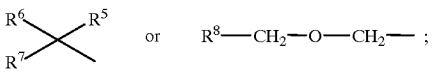

in which $R^5$ and $R^6$ together form a carbonyl group (=O); or
$R^5$ represents hydrogen; and
$R^6$ represents halogen or hydroxyl; or
$R^5$ and $R^6$ both represent hydrogen;
$R^7$ and $R^8$ are identical or different and represent phenyl, naphthyl, benzothiazolyl, quinolyl, pyrimidyl or pyridyl which are optionally substituted 1 to 4 times by identical or different substituents selected from the group consisting of halogen, trifluoromethyl, nitro, cyano, trifluoromethoxy, and radicals of the formula —$SO_2$—$CH_3$ or —$NR^9R^{10}$;
in which $R^9$ and $R^{10}$ are identical or different and represent hydrogen or straight-chain or branched alkyl having 1 to 3 carbon atoms;

E represents cycloalkyl having 3 to 6 carbon atoms, or straight-chain or branched alkyl having 1 to 8 carbon atoms;

$R^1$ represents hydroxyl;

$R^2$ represents methyl;

$R^3$ and $R^4$ are identical or different and represent straight-chain or branched alkyl having 1 to 3 carbon atoms; or $R^3$ and $R^4$ together form a spiro-linked alkyl chain having 2 to 4 carbon atoms; or a salt or N-oxide thereof.

2. A tetrahydroquinoline of the formula (I) according to claim 1, in which

A represents phenyl which is optionally substituted 1 to 2 times by identical or different substituents selected from the group consisting of fluorine, chlorine, trifluoromethyl, methyl, ethyl, methoxy and ethoxy;

D represents a radical of the formula:

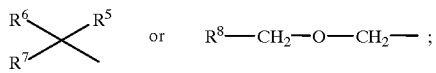

in which $R^5$ and $R^6$ together form a carbonyl group (=O); or $R^5$ represents hydrogen; and $R^6$ represents fluorine or hydroxyl; or $R^5$ and $R^6$ both represent hydrogen;

$R^7$ and $R^8$ are identical or different and represent phenyl, naphthyl, benzothiazolyl, quinolyl, pyrimidyl or pyridyl which are optionally substituted 1 to 3 times by identical or different substituents selected from the group consisting of fluorine, chlorine, bromine, trifluoromethyl, nitro, cyano, trifluoromethoxy, amino or dimethylamino;

E represents cyclopropyl, cyclobutyl, cyclopentyl, or straight-chain or branched alkyl having 1 to 6 carbon atoms;

$R^1$ represents hydroxyl;

$R^2$ represents methyl;

$R^3$ and $R^4$ represent methyl; or $R^3$ and $R^4$ together form a spiro-linked cyclopropyl, cyclobutyl or cyclopentyl ring;

or a salt or N-oxide thereof.

3. A tetrahydroquinoline of the formula (I) according to claim 1, in which

A represents phenyl which is optionally substituted 1 to 2 times by identical or different substituents selected from the group consisting of fluorine, chlorine, trifluoromethyl, methyl, methoxy and ethoxy;

D represents a radical of the formula:

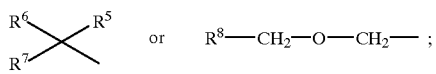

in which $R^5$ and $R^6$ together form a carbonyl group (=O); or $R^5$ represents hydrogen; and $R^6$ represents fluorine or hydroxyl; or $R^5$ and $R^6$ both represent hydrogen;

$R^7$ and $R^8$ are identical or different and represent phenyl, naphthyl, benzothiazolyl, quinolyl, pyrimidyl or pyridyl which are optionally substituted 1 to 3 times by identical or different substituents selected from the group consisting of fluorine, chlorine, bromine, trifluoromethyl, nitro, cyano, trifluoromethoxy, amino or dimethylamino;

E represents cyclopropyl, cyclopentyl, or straight-chain or branched alkyl having 1 to 3 carbon atoms;

$R^1$ represents hydroxyl;

$R^2$ represents methyl;

$R^3$ and $R^4$ represent methyl; or $R^3$ and $R^4$ together form a spiro-linked cyclopropyl, cyclobutyl or cyclopentyl ring;

or a salt or N-oxide thereof.

4. A tetrahydroquinoline of the formula (I):

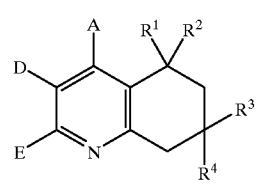

in which

A represents phenyl which is optionally substituted 1 to 2 times by identical or different substituents selected from the group consisting of halogen, trifluoromethyl and straight-chain or branched alkyl or alkoxy having in each case 1 to 3 carbon atoms;

D represents a radical of the formula:

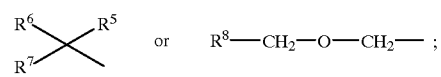

in which $R^5$ and $R^6$ together form a carbonyl group (=O); or $R^5$ represents hydrogen; and $R^6$ represents halogen or hydroxyl; or $R^5$ and $R^6$ both represent hydrogen;

$R^7$ and $R^8$ are identical or different and represent benzothiazolyl, quinolyl, pyrimidyl or pyridyl which are optionally substituted 1 to 4 times by identical or different substituents selected from the group consisting of halogen, trifluoromethyl, nitro, cyano, trifluoromethoxy, and radicals of the formula —$SO_2$—$CH_3$ or —$NR^9R^{10}$;

in which $R^9$ and $R^{10}$ are identical or different and represent hydrogen or straight-chain or branched alkyl having 1 to 3 carbon atoms;

E represents cycloalkyl having 3 to 6 carbon atoms, or straight-chain or branched alkyl having 1 to 8 carbon atoms;

$R^1$ represents hydroxyl;

$R^2$ represents hydrogen or methyl;

$R^3$ and $R^4$ are identical or different and represent straight-chain or branched alkyl having 1 to 3 carbon atoms; or $R^3$ and $R^4$ together form a spiro-linked alkyl chain having 2 to 4 carbon atoms;

or a salt or N-oxide thereof.

5. A tetrahydroquinoline of the formula (I) according to claim 4, in which

A represents phenyl which is optionally substituted 1 to 2 times by identical or different substituents selected from the group consisting of fluorine, chlorine, trifluoromethyl, methyl, ethyl, methoxy and ethoxy;

D represents a radical of the formula:

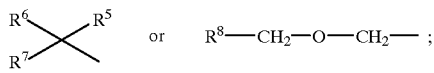

in which

R$^5$ and R$^6$ together form a carbonyl group (=O); or

R$^5$ represents hydrogen; and

R$^6$ represents fluorine or hydroxyl; or

R$^5$ and R$^6$ both represent hydrogen;

R$^7$ and R$^8$ are identical or different and represent benzothiazolyl, quinolyl, pyrimidyl or pyridyl which are optionally substituted 1 to 3 times by identical or different substituents selected from the group consisting of fluorine, chlorine, bromine, trifluoromethyl, nitro, cyano, trifluoromethoxy, amino or dimethylamino;

E represents cyclopropyl, cyclobutyl, cyclopentyl, or straight-chain or branched alkyl having 1 to 6 carbon atoms;

R$^1$ represents hydroxyl;

R$^2$ represents hydrogen or methyl;

R$^3$ and R$^4$ represent methyl; or

R$^3$ and R$^4$ together form a spiro-linked cyclopropyl, cyclobutyl or cyclopentyl ring;

or a salt or N-oxide thereof.

6. A tetrahydroquinoline of the formula (I) according to claim 4, in which

A represents phenyl which is optionally substituted 1 to 2 times by identical or different substituents selected from the group consisting of fluorine, chlorine, trifluoromethyl, methyl, methoxy and ethoxy;

D represents a radical of the formula:

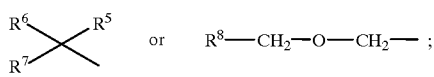

in which

R$^5$ and R$^6$ together form a carbonyl group (=O); or

R$^5$ represents hydrogen; and

R$^6$ represents fluorine or hydroxyl; or

R$^5$ and R$^6$ both represent hydrogen;

R$^7$ and R$^8$ are identical or different and represent benzothiazolyl, quinolyl, pyrimidyl or pyridyl which are optionally substituted 1 to 3 times by identical or different substituents selected from the group consisting of fluorine, chlorine, bromine, trifluoromethyl, nitro, cyano, trifluoromethoxy, amino or dimethylamino;

E represents cyclopropyl, cyclopentyl, or straight-chain or branched alkyl having 1 to 3 carbon atoms;

R$^1$ represents hydroxyl;

R$^2$ represents hydrogen or methyl;

R$^3$ and R$^4$ represent methyl; or

R$^3$ and R$^4$ together form a spiro-linked cyclopropyl, cyclobutyl or cyclopentyl ring;

or a salt or N-oxide thereof.

7. A tetrahydroquinoline of the formula (I):

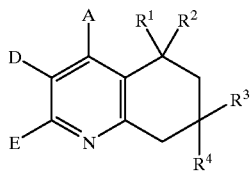

(I)

in which

A represents phenyl which is optionally substituted 1 to 2 times by identical or different substituents selected from the group consisting of chlorine, trifluoromethyl and straight-chain or branched alkyl or alkoxy having in each case 1 to 3 carbon atoms, or represents phenyl disubstituted by fluorine, or represents 3-fluorophenyl;

D represents a radical of the formula:

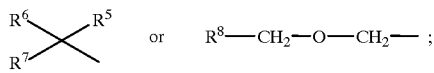

in which

R$^5$ and R$^6$ together form a carbonyl group (=O); or

R$^5$ represents hydrogen; and

R$^6$ represents halogen or hydroxyl; or

R$^5$ and R$^6$ both represent hydrogen;

R$^7$ and R$^8$ are identical or different and represent phenyl, naphthyl, benzothiazolyl, quinolyl, pyrimidyl or pyridyl which are optionally substituted 1 to 4 times by identical or different substituents selected from the group consisting of halogen, trifluoromethyl, nitro, cyano, trifluoromethoxy, and radicals of the formula —SO$_2$—CH$_3$ or —NR$^9$R$^{10}$;

in which

R$^9$ and R$^{10}$ are identical or different and represent hydrogen or straight-chain or branched alkyl having 1 to 3 carbon atoms;

E represents cycloalkyl having 3 to 6 carbon atoms, or straight-chain or branched alkyl having 1 to 8 carbon atoms;

R$^1$ represents hydroxyl;

R$^2$ represents hydrogen or methyl;

R$^3$ and R$^4$ are identical or different and represent straight-chain or branched alkyl having 1 to 3 carbon atoms; or R$^3$ and R$^4$ together form a spiro-linked alkyl chain having 2 to 4 carbon atoms;

or a salt or N-oxide thereof.

8. A tetrahydroquinoline of the formula (I) according to claim 7, in which

A represents phenyl which is optionally substituted 1 to 2 times by identical or different substituents selected from the group consisting of chlorine, trifluoromethyl, methyl, ethyl, methoxy and ethoxy, or represents phenyl disubstituted by fluorine, or represents 3-fluorophenyl;

D represents a radical of the formula:

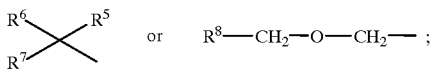

in which
R⁵ and R⁶ together form a carbonyl group (=O); or
R⁵ represents hydrogen; and
R⁶ represents fluorine or hydroxyl; or
R⁵ and R⁶ both represent hydrogen;
R⁷ and R⁸ are identical or different and represent phenyl, naphthyl, benzothiazolyl, quinolyl, pyrimidyl or pyridyl which are optionally substituted 1 to 3 times by identical or different substituents selected from the group consisting of fluorine, chlorine, bromine, trifluoromethyl, nitro, cyano, trifluoromethoxy, amino or dimethylamino;
E represents cyclopropyl, cyclobutyl, cyclopentyl, or straight-chain or branched alkyl having 1 to 6 carbon atoms;
$R^1$ represents hydroxyl;
$R^2$ represents hydrogen or methyl;
$R^3$ and $R^4$ represent methyl; or
$R^3$ and $R^4$ together form a spiro-linked cyclopropyl, cyclobutyl or cyclopentyl ring;
or a salt or N-oxide thereof.

9. A tetrahydroquinoline of the formula (I) according to claim 7, in which
A represents phenyl which is optionally substituted 1 to 2 times by identical or different substituents selected from the group consisting of chlorine, trifluoromethyl, methyl, methoxy and ethoxy, or represents phenyl disubstituted by fluorine, or represents 3-fluorophenyl;
D represents a radical of the formula:

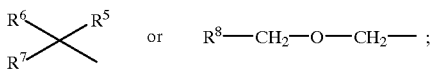

in which
R⁵ and R⁶ together form a carbonyl group (=O); or
R⁵ represents hydrogen; and
R⁶ represents fluorine or hydroxyl; or
R⁵ and R⁶ both represent hydrogen;
R⁷ and R⁸ are identical or different and represent phenyl, naphthyl, benzothiazolyl, quinolyl, pyrimidyl or pyridyl which are optionally substituted 1 to 3 times by identical or different substituents selected from the group consisting of fluorine, chlorine, bromine, trifluoromethyl, nitro, cyano, trifluoromethoxy, amino or dimethylamino;
E represents cyclopropyl, cyclopentyl, or straight-chain or branched alkyl having 1 to 3 carbon atoms;
$R^1$ represents hydroxyl;
$R^2$ represents hydrogen or methyl;
$R^3$ and $R^4$ represent methyl; or
$R^3$ and $R^4$ together form a spiro-linked cyclopropyl, cyclobutyl or cyclopentyl ring;
or a salt or N-oxide thereof.

10. A tetrahydroquinoline of the formula (I):

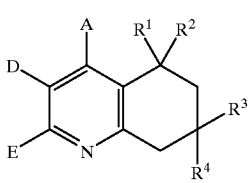

(I)

in which
A represents phenyl which is optionally substituted 1 to 2 times by identical or different substituents selected from the group consisting of halogen, trifluoromethyl and straight-chain or branched alkyl or alkoxy having in each case 1 to 3 carbon atoms;
D represents a radical of the formula:

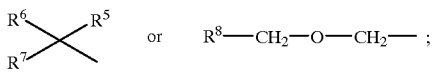

in which
R⁵ and R⁶ together form a carbonyl group (=O); or
R⁵ represents hydrogen; and
R⁶ represents halogen or hydroxyl; or
R⁵ and R⁶ both represent hydrogen;
R⁷ and R⁸ are identical or different and represent phenyl, naphthyl, benzothiazolyl, quinolyl, pyrimidyl or pyridyl which are optionally substituted 1 to 4 times by identical or different substituents selected from the group consisting of halogen, nitro, cyano, trifluoromethoxy, and radicals of the formula —SO₂—CH₃ or —NR⁹R¹⁰;
in which
R⁹ and R¹⁰ are identical or different and represent hydrogen or straight-chain or branched alkyl having 1 to 3 carbon atoms;
E represents cycloalkyl having 3 to 6 carbon atoms, or straight-chain or branched alkyl having 1 to 8 carbon atoms;
$R^1$ represents hydroxyl;
$R^2$ represents hydrogen or methyl;
$R^3$ and $R^4$ together form a spiro-linked alkyl chain having 2 to 4 carbon atoms;
or a salt or N-oxide thereof.

11. A tetrahydroquinoline of the formula (I) according to claim 10, in which
A represents phenyl which is optionally substituted 1 to 2 times by identical or different substituents selected from the group consisting of fluorine, chlorine, trifluoromethyl, methyl, ethyl, methoxy and ethoxy;
D represents a radical of the formula:

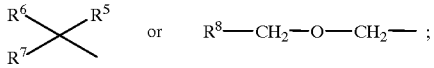

in which
R⁵ and R⁶ together form a carbonyl group (=O); or
R⁵ represents hydrogen; and
R⁶ represents fluorine or hydroxyl; or
R⁵ and R⁶ both represent hydrogen;
R⁷ and R⁸ are identical or different and represent phenyl, naphthyl, benzothiazolyl, quinolyl, pyrimidyl or pyridyl which are optionally substituted 1 to 3 times by identical or different substituents selected from the group consisting of fluorine, chlorine, bromine, nitro, cyano, trifluoromethoxy, amino or dimethylamino;

E represents cyclopropyl, cyclobutyl, cyclopentyl, or straight-chain or branched alkyl having 1 to 6 carbon atoms;

$R^1$ represents hydroxyl;

$R^2$ represents hydrogen or methyl;

$R^3$ and $R^4$ together form a spiro-linked cyclopropyl, cyclobutyl or cyclopentyl ring;

or a salt or N-oxide thereof.

12. A tetrahydroquinoline of the formula (I) according to claim 10, in which

A represents phenyl which is optionally substituted 1 to 2 times by identical or different substituents selected from the group consisting of fluorine, chlorine, trifluoromethyl, methyl, methoxy and ethoxy;

D represents a radical of the formula:

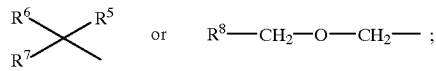

in which $R^5$ and $R^6$ together form a carbonyl group (=O); or $R^5$ represents hydrogen; and $R^6$ represents fluorine or hydroxyl; or $R^5$ and $R^6$ both represent hydrogen;

$R^7$ and $R^8$ are identical or different and represent phenyl, naphthyl, benzothiazolyl, quinolyl, pyrimidyl or pyridyl which are optionally substituted 1 to 3 times by identical or different substituents selected from the group consisting of fluorine, chlorine, bromine, nitro, cyano, trifluoromethoxy, amino or dimethylamino;

E represents cyclopropyl, cyclopentyl, or straight-chain or branched alkyl having 1 to 3 carbon atoms;

$R^1$ represents hydroxyl;

$R^2$ represents hydrogen or methyl;

$R^3$ and $R^4$ together form a spiro-linked cyclopropyl, cyclobutyl or cyclopentyl ring;

or a salt or N-oxide thereof.

13. A tetrahydroquinoline of the formula (I):

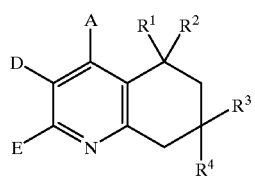

(I)

in which

A represents phenyl which is optionally substituted 1 to 2 times by identical or different substituents selected from the group consisting of halogen, trifluoromethyl and straight-chain or branched alkyl or alkoxy having in each case 1 to 3 carbon atoms;

D represents a radical of the formula:

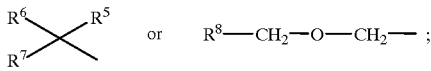

in which $R^5$ and $R^6$ together form a carbonyl group (=O); or $R^5$ represents hydrogen; and $R^6$ represents halogen or hydroxyl; or $R^5$ and $R^6$ both represent hydrogen;

$R^7$ and $R^8$ are identical or different and represent phenyl, naphthyl, benzothiazolyl, quinolyl, pyrimidyl or pyridyl which are optionally substituted 2 to 4 times by identical or different substituents selected from the group consisting of bromine, trifluoromethyl, nitro, cyano, trifluoromethoxy, and radicals of the formula —$SO_2$—$CH_3$ or —$NR^9R^{10}$, or which are optionally trisubstituted by fluorine;

in which $R^9$ and $R^{10}$ are identical or different and represent hydrogen or straight-chain or branched alkyl having 1 to 3 carbon atoms;

E represents cycloalkyl having 3 to 6 carbon atoms, or straight-chain or branched alkyl having 1 to 8 carbon atoms;

$R^1$ represents hydroxyl;

$R^2$ represents hydrogen or methyl;

$R^3$ and $R^4$ are identical or different and represent straight-chain or branched alkyl having 1 to 3 carbon atoms; or $R^3$ and $R^4$ together form a spiro-linked alkyl chain having 2 to 4 carbon atoms;

or a salt or N-oxide thereof.

14. A tetrahydroquinoline of the formula (I) according to claim 13, in which

A represents phenyl which is optionally substituted 1 to 2 times by identical or different substituents selected from the group consisting of fluorine, chlorine, trifluoromethyl, methyl, ethyl, methoxy and ethoxy;

D represents a radical of the formula:

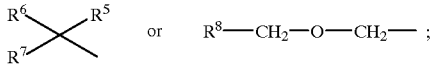

in which $R^5$ and $R^6$ together form a carbonyl group (=O); or $R^5$ represents hydrogen; and $R^6$ represents fluorine or hydroxyl; or $R^5$ and $R^6$ both represent hydrogen;

$R^7$ and $R^8$ are identical or different and represent phenyl, naphthyl, benzothiazolyl, quinolyl, pyrimidyl or pyridyl which are optionally substituted 2 or 3 times by identical or different substituents selected from the group consisting of bromine, trifluoromethyl, nitro, cyano, trifluoromethoxy, amino or dimethylamino, or which are optionally trisubstituted by fluorine;

E represents cyclopropyl, cyclobutyl, cyclopentyl, or straight-chain or branched alkyl having 1 to 6 carbon atoms;

$R^1$ represents hydroxyl;

$R^2$ represents hydrogen or methyl;

$R^3$ and $R^4$ represent methyl; or $R^3$ and $R^4$ together form a spiro-linked cyclopropyl, cyclobutyl or cyclopentyl ring;

or a salt or N-oxide thereof.

15. A tetrahydroquinoline of the formula (I) according to claim 13, in which

A represents phenyl which is optionally substituted 1 to 2 times by identical or different substituents selected from the group consisting of fluorine, chlorine, trifluoromethyl, methyl, methoxy and ethoxy;

D represents a radical of the formula:

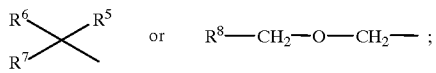

in which $R^5$ and $R^6$ together form a carbonyl group (=O); or $R^5$ represents hydrogen; and $R^6$ represents fluorine or hydroxyl; or $R^5$ and $R^6$ both represent hydrogen;

$R^7$ and $R^8$ are identical or different and represent phenyl, naphthyl, benzothiazolyl, quinolyl, pyrimidyl or pyridyl which are optionally substituted 2 or 3 times by identical or different substituents selected from the group consisting of bromine, trifluoromethyl, nitro, cyano, trifluoromethoxy, amino or dimethylamino, or which are optionally trisubstituted by fluorine;

E represents cyclopropyl, cyclopentyl, or straight-chain or branched alkyl having 1 to 3 carbon atoms;

$R^1$ represents hydroxyl;

$R^2$ represents hydrogen or methyl;

$R^3$ and $R^4$ represent methyl; or $R^3$ and $R^4$ together form a spiro-linked cyclopropyl, cyclobutyl or cyclopentyl ring;

or a salt or N-oxide thereof.

16. A pharmaceutical composition comprising at least one compound of the formula (I) or a salt or N-oxide thereof according to any one of claims 1–15 and an inert, non-toxic, pharmaceutically suitable carrier or solvent.

17. A method of preventing or treating a condition in a patient comprising administering to said patient an amount effective to prevent or treat said condition of at least one compound of the formula (I) or a salt or N-oxide thereof according to any one of claims 1–15, said condition being selected from hyperlipoproteinaemias, dyslipidaemias, hypertriglyceridaemias, hyperlipidaemias or arteriosclerosis.

* * * * *